(12) United States Patent
Courtney et al.

(10) Patent No.: US 8,712,506 B2
(45) Date of Patent: *Apr. 29, 2014

(54) MEDICAL IMAGING PROBE WITH ROTARY ENCODER

(75) Inventors: Brian Courtney, Toronto (CA); Nigel Robert Munce, Toronto (CA); Amandeep Singh Thind, Toronto (CA); Victor Xiao Dong Yang, Toronto (CA); Francis Stuart Foster, Toronto (CA)

(73) Assignee: Sunnybrook Health Sciences Centre (CA)

( * ) Notice: Subject to any disclaimer, the term of this patent is extended or adjusted under 35 U.S.C. 154(b) by 1300 days.

This patent is subject to a terminal disclaimer.

(21) Appl. No.: 12/010,207

(22) Filed: Jan. 22, 2008

(65) Prior Publication Data

US 2008/0177139 A1      Jul. 24, 2008

Related U.S. Application Data

(60) Provisional application No. 60/881,169, filed on Jan. 19, 2007.

(51) Int. Cl.
*A61B 1/00* (2006.01)

(52) U.S. Cl.
USPC ........... 600/478; 600/427; 600/467; 600/476; 385/25; 250/231.18

(58) Field of Classification Search
USPC ......... 600/137, 160, 178, 459, 462, 463, 466, 600/407, 476, 478, 427, 473; 606/39, 606/45–46, 85, 180, 239
See application file for complete search history.

(56) References Cited

U.S. PATENT DOCUMENTS

| 4,093,991 | A | * | 6/1978 | Christie et al. ................ 356/319 |
| 4,697,577 | A | | 10/1987 | Forkner |
| 4,794,931 | A | | 1/1989 | Yock |
| 4,869,258 | A | | 9/1989 | Hetz |
| 4,895,158 | A | | 1/1990 | Kawabuchi et al. |
| 4,951,677 | A | | 8/1990 | Crowley |
| 4,972,839 | A | | 11/1990 | Angelsen |
| 5,129,725 | A | * | 7/1992 | Ishizuka et al. ................ 356/617 |
| 5,152,293 | A | | 10/1992 | Vonesh et al. |

(Continued)

FOREIGN PATENT DOCUMENTS

| WO | 03/067526 | 8/2003 |
| WO | 2004/010856 | 2/2004 |

(Continued)

OTHER PUBLICATIONS

M. L. Dufour, G. Lamouche, S. Vergnole, B. Gauthier, C. Padioleau, M. Hewko, S. Levesque, and V. Bartulovic, "Surface inspection of hard to reach industrial parts using low-coherence interferometry", Proc. SPIE Int. Soc. Opt. Eng., 6343, 63431Z, pp. 1-7. 2006.*

(Continued)

*Primary Examiner* — Unsu Jung
*Assistant Examiner* — Daniel Huntley

(57) ABSTRACT

The present invention provides minimally invasive imaging probe having an optical encoder integrated therewith for accurately measuring or estimating the rotational velocity near the distal end of the medical device, such as an imaging probe which undergoes rotational movement during scanning of surrounding tissue in bodily lumens and cavities.

33 Claims, 22 Drawing Sheets

(56) References Cited

U.S. PATENT DOCUMENTS

| | | | |
|---|---|---|---|
| 5,373,845 | A | 12/1994 | Gardineer |
| 5,373,849 | A | 12/1994 | Maroney |
| 5,375,602 | A | 12/1994 | Lancee |
| 5,379,772 | A | 1/1995 | Imran |
| 5,427,107 | A | 6/1995 | Milo |
| 5,429,136 | A | 7/1995 | Milo |
| 5,465,724 | A | 11/1995 | Sliwa, Jr. et al. |
| 5,469,853 | A | 11/1995 | Law et al. |
| 5,485,845 | A | 1/1996 | Verdonk |
| 5,505,088 | A | 4/1996 | Chandraratna et al. |
| 5,506,681 | A * | 4/1996 | Igaki .......................... 356/616 |
| 5,507,292 | A * | 4/1996 | Jang et al. ................... 600/467 |
| 5,606,975 | A | 3/1997 | Liang |
| 5,647,367 | A | 7/1997 | Lum et al. |
| 5,651,366 | A | 7/1997 | Liang |
| 5,682,895 | A | 11/1997 | Ishiguro |
| 5,718,231 | A | 2/1998 | Dewhurst |
| 5,779,643 | A | 7/1998 | Lum et al. |
| 5,817,021 | A | 10/1998 | Reichenberger |
| 6,035,229 | A | 3/2000 | Silverstein |
| 6,110,121 | A | 8/2000 | Lenker |
| 6,134,003 | A | 10/2000 | Tearney |
| 6,171,247 | B1 | 1/2001 | Seward et al. |
| 6,178,346 | B1 | 1/2001 | Amundson |
| 6,200,268 | B1 | 3/2001 | Vince |
| 6,264,610 | B1 | 7/2001 | Zhu |
| 6,315,732 | B1 | 11/2001 | Suorsa |
| 6,390,978 | B1 | 5/2002 | Irion et al. |
| 6,445,939 | B1 | 9/2002 | Swanson et al. |
| 6,450,964 | B1 | 9/2002 | Webler |
| 6,485,413 | B1 | 11/2002 | Boppart |
| 6,592,526 | B1 | 7/2003 | Lenker |
| 6,626,834 | B2 | 9/2003 | Dunne et al. |
| 6,690,958 | B1 | 2/2004 | Walker et al. |
| 6,949,072 | B2 | 9/2005 | Furnish et al. |
| 6,975,898 | B2 | 12/2005 | Seibel |
| 7,077,808 | B2 | 7/2006 | Couvillon |
| 7,289,842 | B2 | 10/2007 | Maschke |
| 7,366,376 | B2 | 4/2008 | Shishkov et al. |
| 7,761,139 | B2 | 7/2010 | Tearney et al. |
| 2003/0023019 | A1 | 1/2003 | Kondou |
| 2003/0163049 | A1 * | 8/2003 | Balas .......................... 600/476 |
| 2004/0228013 | A1 * | 11/2004 | Goldstein et al. ............ 359/823 |
| 2005/0020926 | A1 | 1/2005 | Wiklof |
| 2005/0101859 | A1 * | 5/2005 | Maschke ...................... 600/427 |
| 2006/0116571 | A1 | 6/2006 | Maschke |
| 2007/0016062 | A1 | 1/2007 | Park |
| 2007/0161893 | A1 | 7/2007 | Milner |
| 2009/0203991 | A1 | 8/2009 | Papaioannou et al. |

FOREIGN PATENT DOCUMENTS

| | | |
|---|---|---|
| WO | 2004/096049 | 11/2004 |
| WO | 2006/121851 | 11/2006 |
| WO | 2007123518 A1 | 11/2007 |

OTHER PUBLICATIONS

Brezinski et al, "Assessing atherosclerotic plaque morphology: comparison of optical coherence tomography and high frequency intravascular ultrasound", BMJ Heart, May 1997, p. 397-403, vol. 77(5),http://80-gatewayl.ovid.com/lane-proxy.stanford.org/ovidweb.cgi 12 pages.

Nair et al, "Coronary Plaque Classification With Intravascular Ultrasound Radiofrequency Data Analysis", Circulation, 2002;106:2200-2206.

Funovics et al, "Catheter-based in Vivo Imaging of Enzyme Activity and Gene Expression: Feasibility Study in Mice", Radiology, 2004; 231:659-666.

Picano et al, "Angle dependence of ultrasonic backscatter in arterial tissues: a study in vitro", Circulation 1985; 72; pp. 572-576.

Kubo et al, "Assessment of Culprit Lesion Morphology in Acute Myocardial Infarction", J Amer Col Cardiology, vol. 50, No. 10, 2007, pp. 933-939.

Motz et al, "In vivo Raman spectral pathology of human atherosclerosis and vulnerable plaque", J. Bio Optics, 11(2), 021003, Mar./Apr. 2006, 9 pages.

Mao et al, "Graded-index fiber lens proposed for ultrasmall probes used in biomedical imaging", Applied Optics, vol. 46, No. 23, Aug. 10, 2007, pp. 5887-5894.

Klingensmith et al, "Evaluation of Three-Dimensional Segmentation Algorithms for the Identification of Luminal and Medial-Adventitial Borders in Intravascular Ultrasound Images", IEEE Transactions on Medical Imaging, vol. 19, No. 10, Oct. 2000, pp. 996-1011.

Goretz et al, "Contrast Harmonic Intravascular Ultrasound, A Feasibility Study for Vasa Vasorum Imaging", Investigative Radiology, vol. 41, No. 8, Aug. 2006, pp. 631-638.

De Korte et al, "Identification of Atherosclerotic Plaque Components With Intravascular Ultrasound Elastography in Vivo: A Yucatan Pig Study", Circulation, 2002; 105; 1627-1630.

Daniels et al, "Sonoluminescence in Water and Agar Gels During Irradiation With 0.75 MHz Continuous-Wave Ultrasound", Ultrasound in Med. & Biol. vol. 17, No. 3. pp. 297-308, 1991.

Kawasaki et al, "Diagnostic Accuracy of Optical Coherence Tomography and Integrated Backscatter Intravascular Ultrasound Images for Tissue Characterization of Human Coronary Plaques", J. Amer. Col. Cardiology, vol. 48, No. 1, 2006, pp. 81-88.

Courtney et al, "Effects of Transducer Position on Backscattered Intensity in Coronary Arteries", Ultrasound in Med. Biol, vol. 28, No. 1, pp. 81-91, 2002.

Hoff, Harm ten. "Scanning mechanisms for intravascular ultrasound imaging: a flexible approach". Diss. Erasmus University, Rotterdam. 1993. Print: 117-151, 195-199.

Caplan JD et al, "Near-infrared spectroscopy for the detection of vulnerable coronary artery plaques". J Am Coll Cardiol Apr. 18, 2006:47(8Suppl):C92-C96.

Caplan, J. D. et al. "Near-Infrared Spectroscopy for the Detection of Vulnerable Coronary Artery Plaques". J. Am. Coll. Cardiol. 47 (8), Suppl C, C92-C96 (2006).

Hoff. "Scanning Mechanisms for Intravascular Ultrasound Imaging: a flexible approach". Chapter 5, pp. 117-199. Printing and binding: Universiteitsdrukkerij Erasmus Universiteit Rotterdam. CIP-Data Koninklijke Bibiliotheek, Den Hagg. Hoff, Harm ten. Thesis Rotterdam. ISBN 90-9006072-3. NUG 743. Copyright 1993 by H. ten Hoff, Rotterdam, the Netherlands.

\* cited by examiner

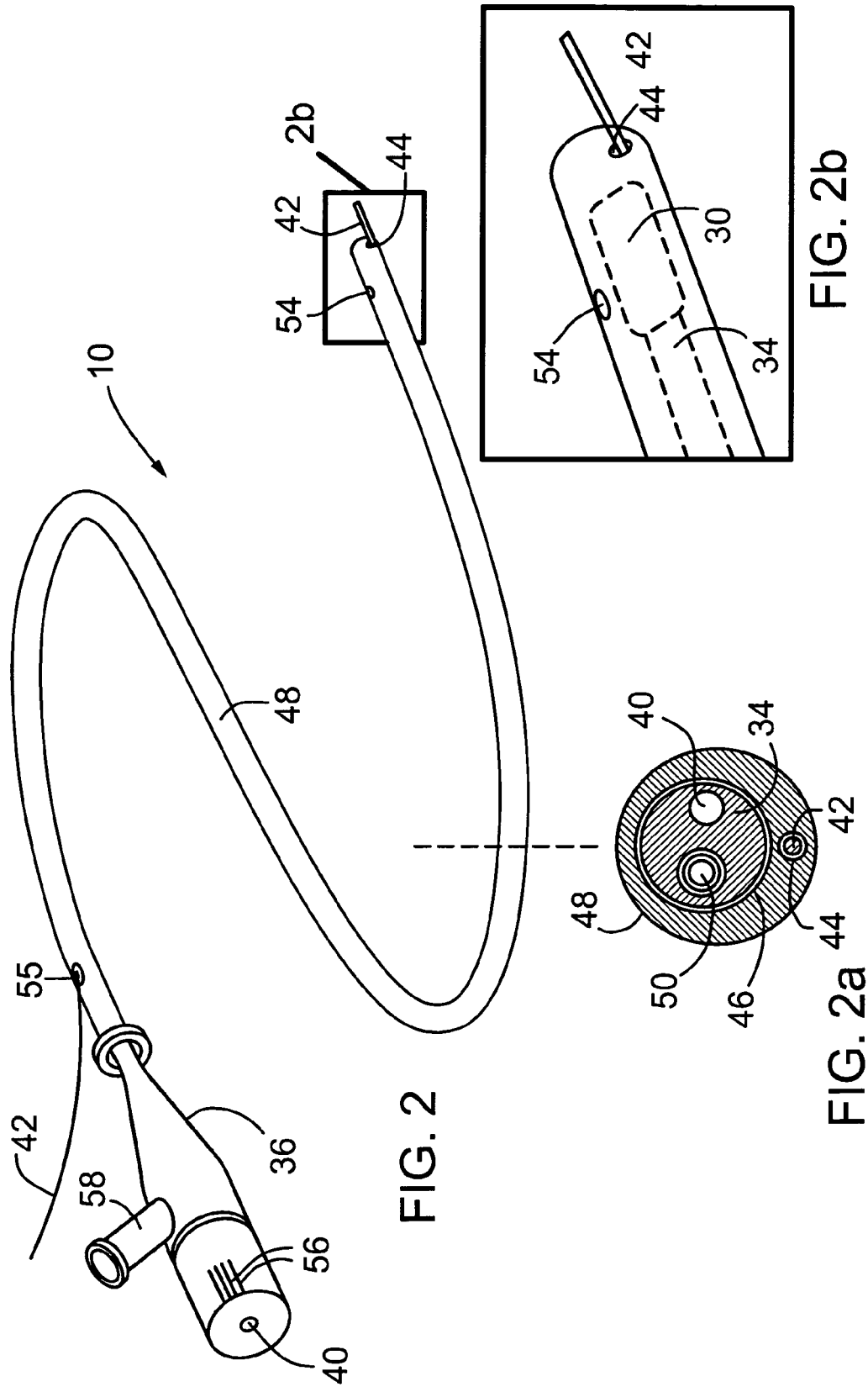

FIG. 2c
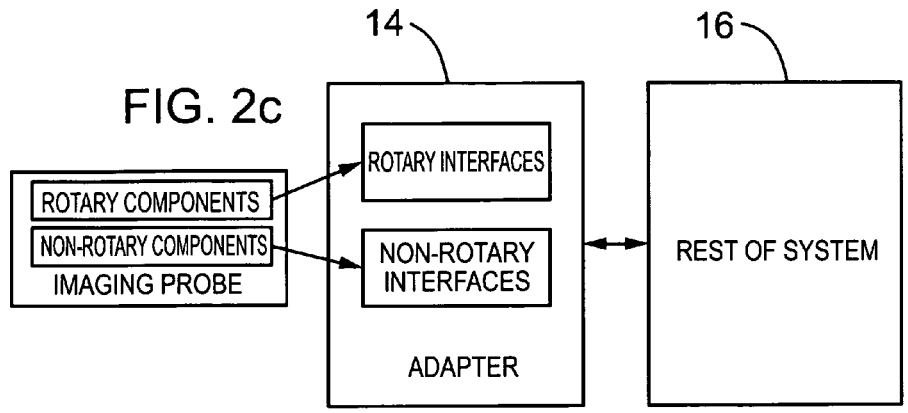
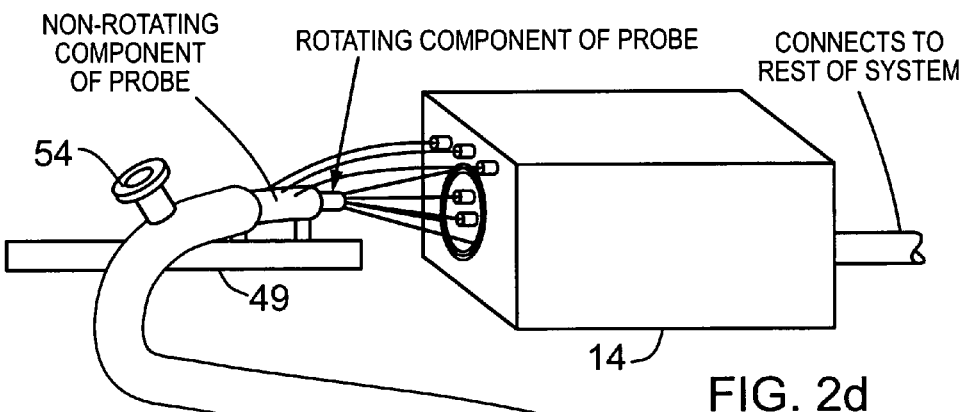
FIG. 2d

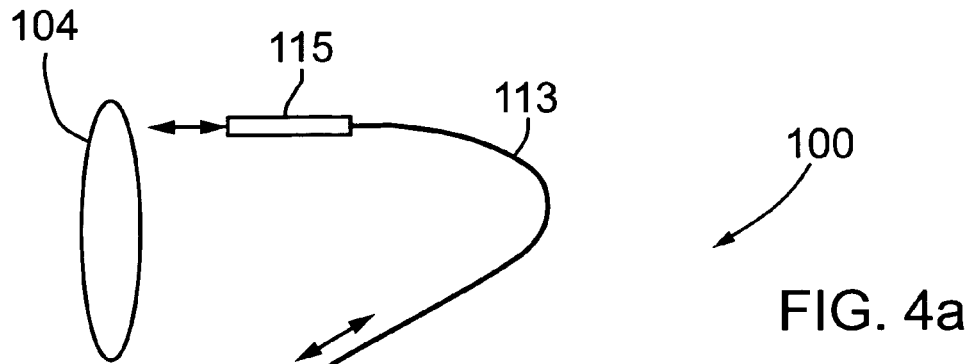
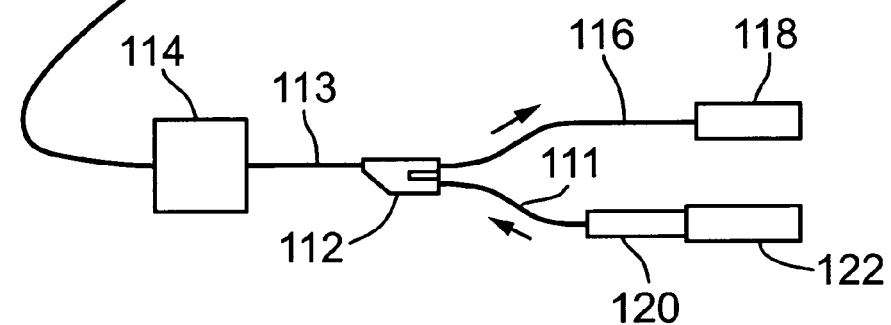
FIG. 4a
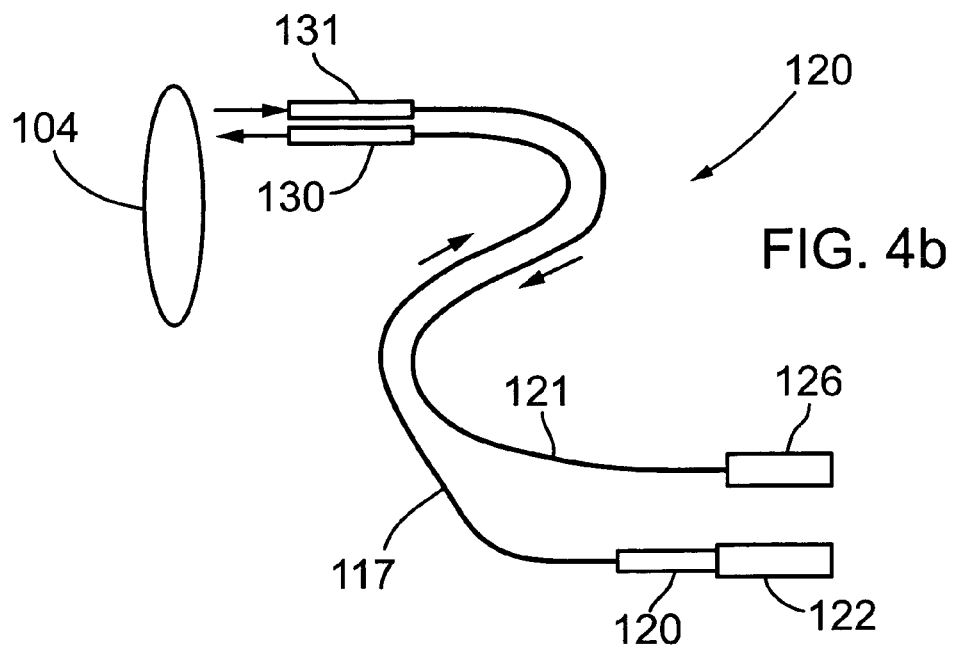
FIG. 4b

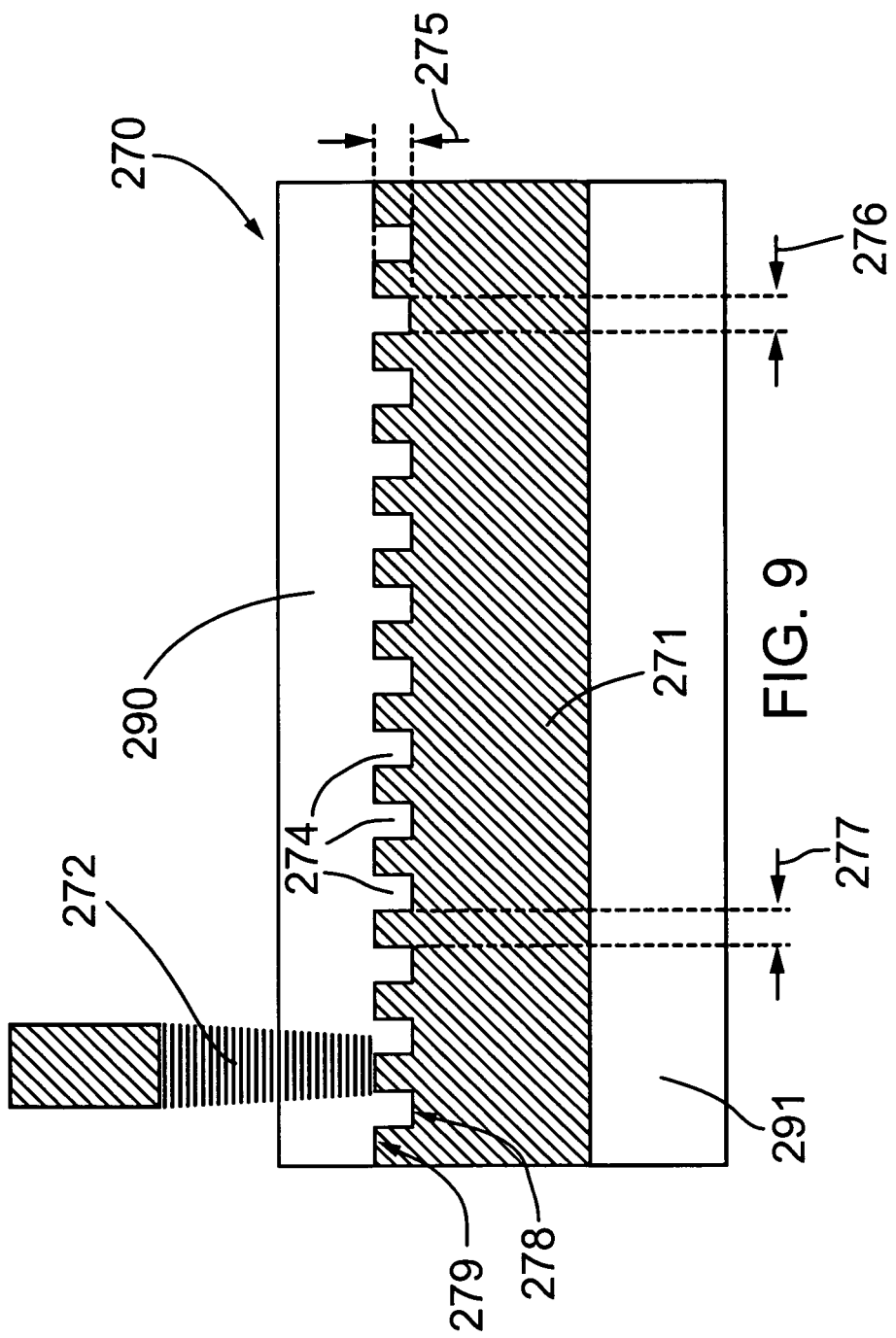

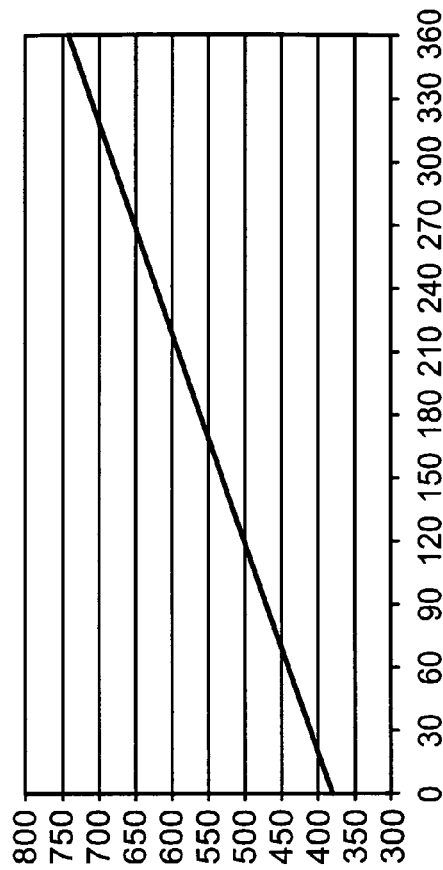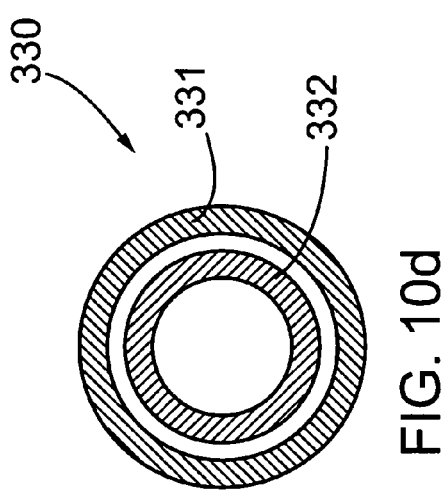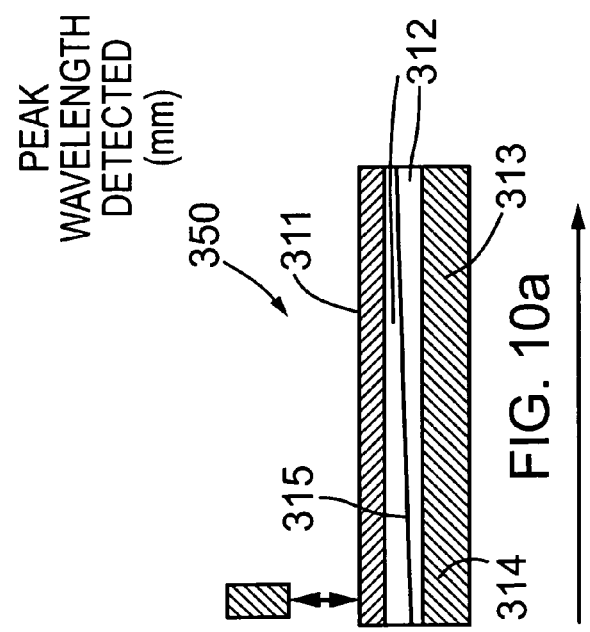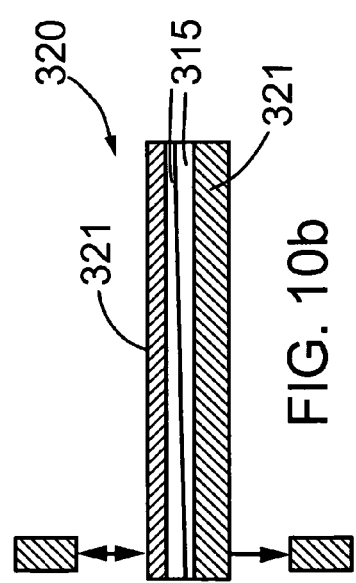

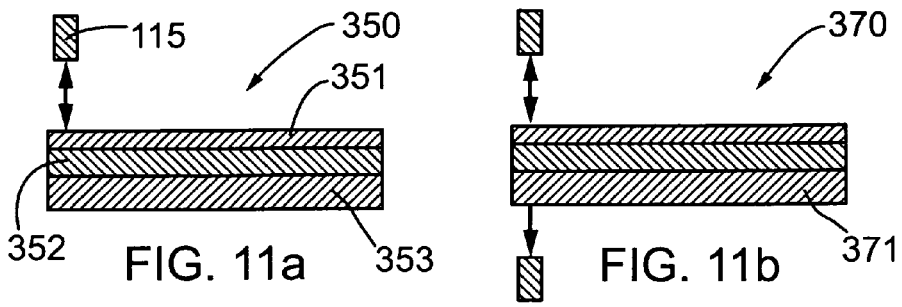
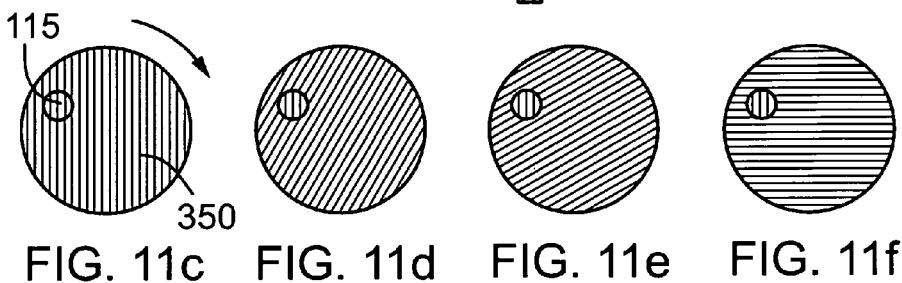
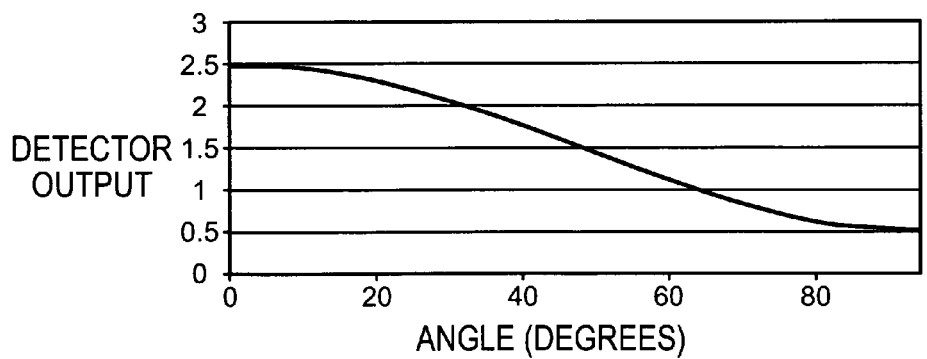
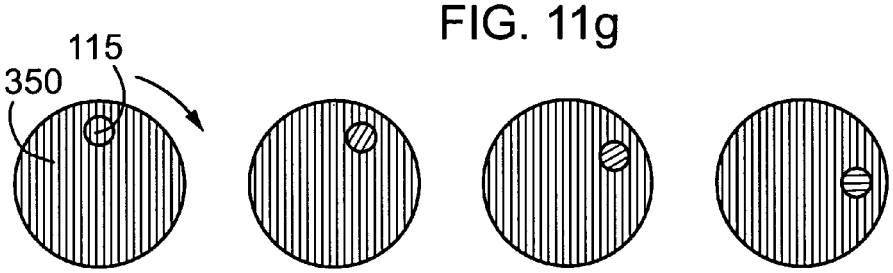

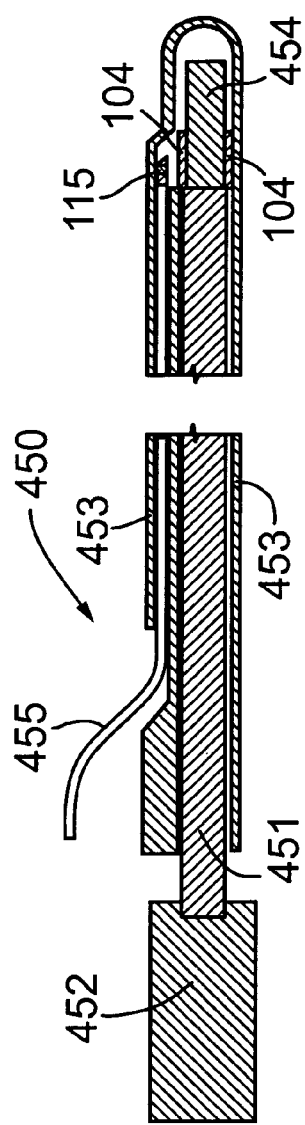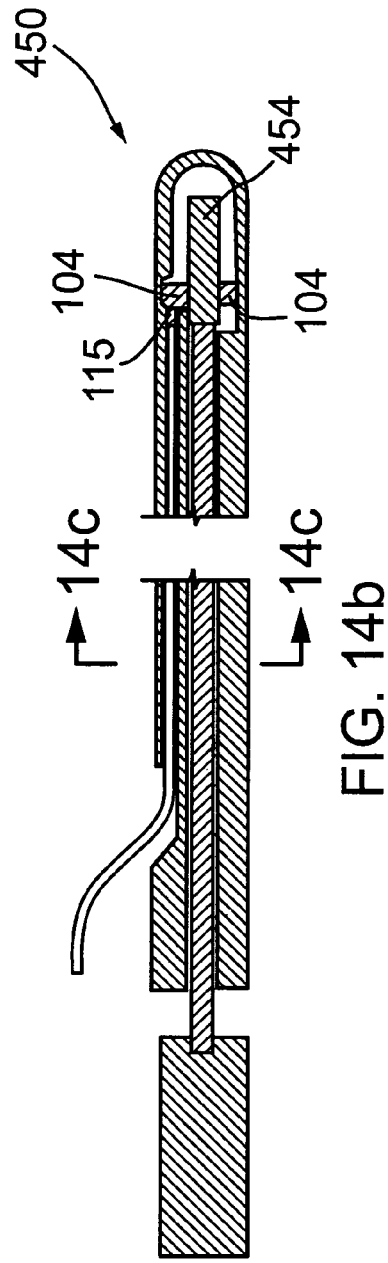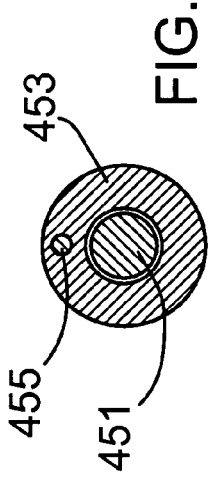
FIG. 14a
FIG. 14b
FIG. 14c

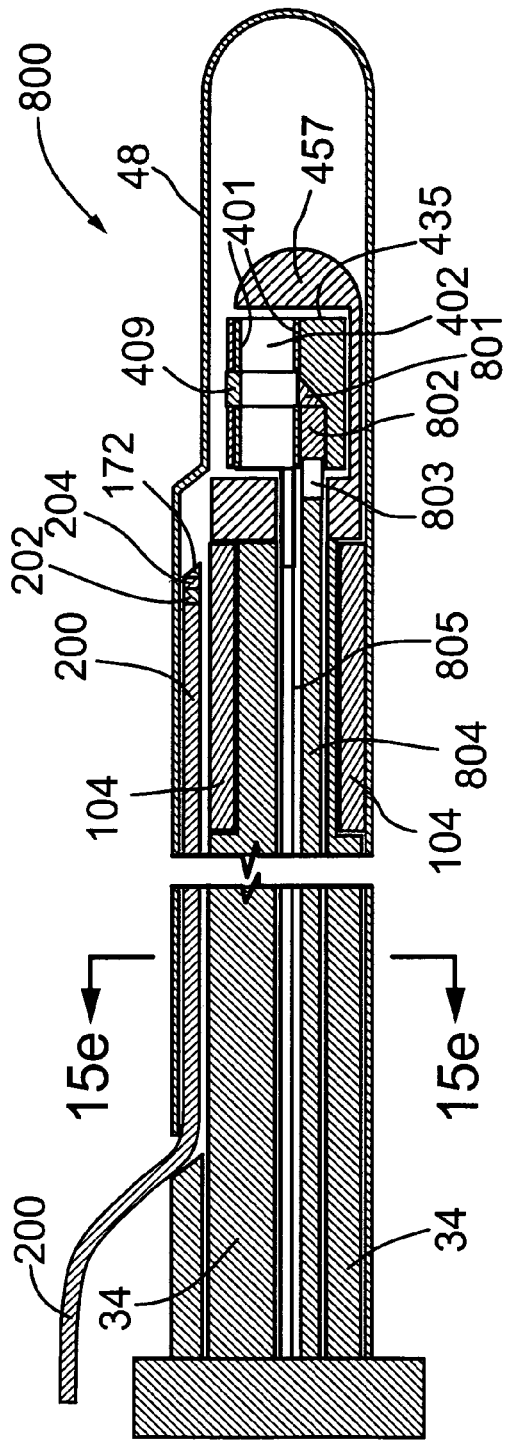
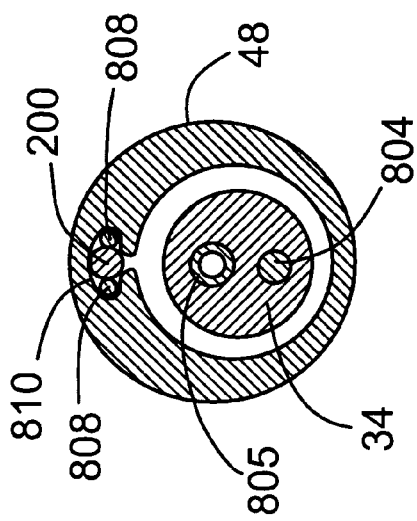
FIG. 15d
FIG. 15e

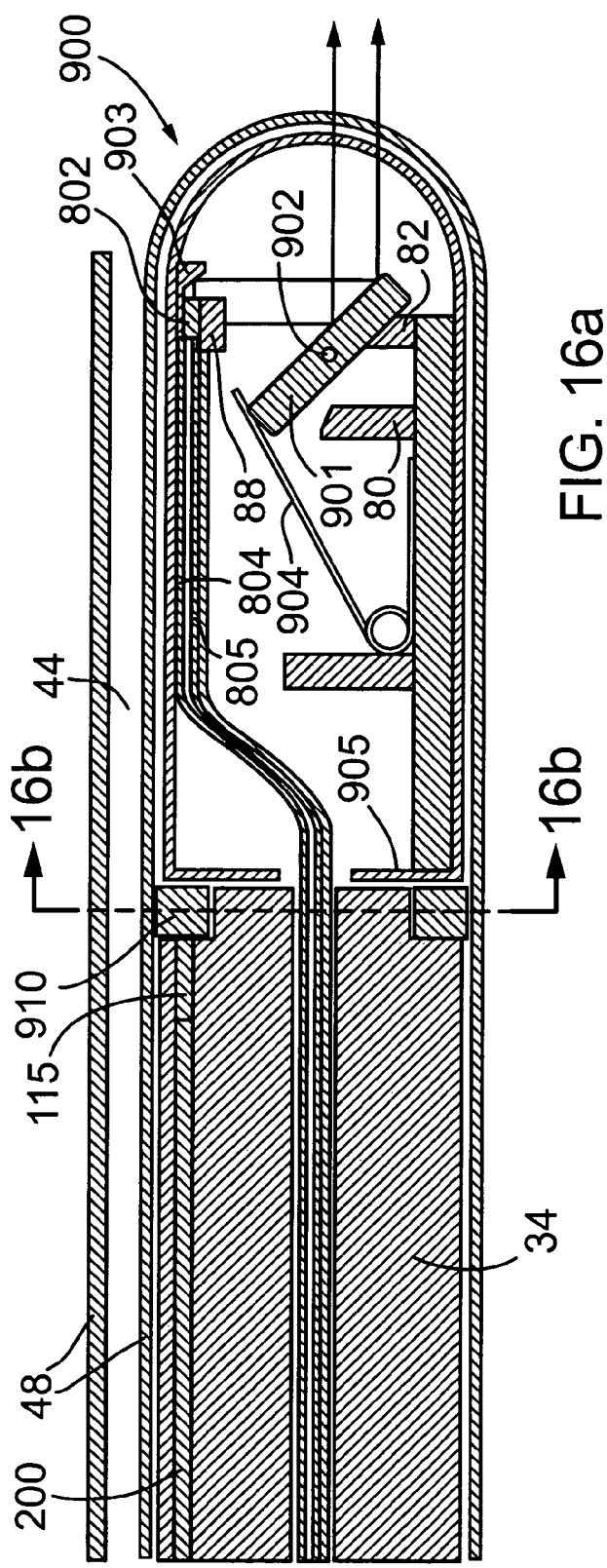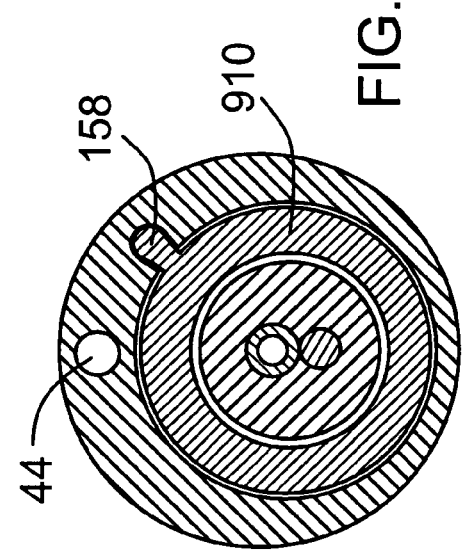

MEDICAL IMAGING PROBE WITH ROTARY ENCODER

CROSS REFERENCE TO RELATED U.S. APPLICATIONS

This patent application relates to, and claims the priority benefit from, U.S. Provisional Patent Application Ser. No. 60/881,169 filed on Jan. 19, 2007, in English, entitled IMAGING PROBE, which is incorporated herein by reference in its entirety.

FIELD OF THE INVENTION

The present invention relates generally to the field of minimally invasive medical devices, including imaging devices for imaging mammalian tissues and structures using high frequency ultrasound (such as intravascular ultrasound or IVUS) and optical imaging methods such as optical coherence tomography (OCT).

BACKGROUND OF THE INVENTION

High resolution imaging of the interior of the body (or for dermatologic or opthalmology applications not restricted to the interior) serves multiple purposes, including any of i) assessing tissue structures and anatomy; ii) planning and/or guiding interventions on localized regions of the body; and iii) assessing the result of interventions that alter the structure, composition or other properties of the localized region. High resolution imaging in this particular case refers to high frequency ultrasound and optical imaging methods. For the purposes of this invention, high frequency ultrasound typically refers to imaging with frequencies of greater than 3 MHz, and more typically in the range of 9 to 100 MHz.

High frequency ultrasound is very useful for intravascular and intracardiac procedures. For these applications, the ultrasound transducers are incorporated into a catheter or other device that can be inserted into the body. By way of example, two particularly important implementations of high frequency ultrasound are intravascular ultrasound (IVUS), for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

Optical imaging methods based on fiber optic technology used in the field of medicine include optical coherence tomography (OCT), angioscopy, near infrared spectroscopy, Raman spectroscopy and fluorescence spectroscopy. These modalities typically require the use of one or more optical fibers to transmit light energy along a shaft between an imaging site and an imaging detector. Optical coherence tomography is an optical analog of ultrasound, and provides imaging resolutions on the order of 1 to 30 microns, but does not penetrate as deeply into tissue as ultrasound in most cases. Fiber optics can also be used to deliver energy for therapeutic maneuvers such as laser ablation of tissue and photodynamic therapy.

Additional forms of imaging related to this invention include angioscopy, endoscopy and other similar imaging mechanisms that involve imaging a site inside the patient using a probe to take pictures based on the back-reflection of light.

High resolution imaging means have been implemented in many forms for assessing several different regions of mammalian anatomy, including the gastrointestinal system, the cardiovascular system (including coronary, peripheral and neurological vasculature), skin, eyes (including the retina), the genitourinary systems, breast tissue, liver tissue and many others. By way of example, imaging of the cardiovascular system with high frequency ultrasound or optical coherence tomography has been developed for assessing the structure and composition of arterial plaque.

High-resolution imaging has been used to measure vessel or plaque geometry, blood flow through diseased arteries, the effect of interventions on arterial plaque (such as by atherectomy, angioplasty and/or stenting). Attempts have also been made using high resolution imaging to identify vascular lesions that have not led to clinical symptoms, but are at increased risk of rupturing or eroding and causing an acute myocardial infarction. These so-called "vulnerable plaques" are an area of interest as the prospect of treating such plaques to pre-empt adverse clinical events is conceptually appealing.

Chronic total occlusions are a specific subset of vascular lesions where the entire lumen of the vessel has been occluded (based on the angiographic appearance of the lesion) for over approximately one month. Most intravascular imaging modalities are "side-viewing" and require passage of an intravascular imaging device through a lesion. In order to image chronic total occlusions, methods of high resolution imaging would be more useful if they were adapted to a "forward-looking" rather than "side-viewing" configuration.

Several of these high resolution imaging means are dependent on the use of a rotary shaft to transmit torque to an imaging device-near the distal end of the probe. These rotary shafts are often long, thin and flexible, such that they can be delivered through anatomical conduits, such as the vasculature, genitourinary tracts, respiratory tracts and other such bodily lumens. Ideally, when a continuous torque is applied to the cable in a specified direction the torque cable develops a property of having a close relation between the degree of rotation at its proximal and distal ends. This allows the simplification of the design of the ultrasound catheter by making the angle of rotation at the distal end of the torque cable (within the body) a reasonable approximation of the angle of rotation at the proximal end of the torque cable (outside of the body).

The rotation of the torque cable or shaft at the point from which the imaging occurs may not be identical to the rotation occurs at the proximal end of the torque cable or shaft. This occurs especially when the flexible shaft is delivered through tortuous passageways and is, at least in part, due to inertia and friction between the rotating components and stationary components of the imaging shaft. The assumption that the rotational speed of the proximal and distal ends of the rotary shaft are equal to each other is also less likely to be valid if the rotational speed varies over time. The undesirable result of not knowing the true angular velocity of the imaging probe at the point from which the imaging beam is directed towards the tissue leads to an artifact referred to non-uniform rotational distortion (NURD). NURD can lead to significant distortion of the image and a concomitant reduction in the geometric accuracy of the image. Knowledge of a more precise estimation of the true rotary speed of the distal rotary shaft or an imaging assembly attached to the rotary shaft can help overcome such distortion by providing more accurate information for image reconstruction. A better estimation of the rotary speed can also help improve the accuracy of co-registration of images when more than one imaging modality is implemented on the imaging probe (such as combined ultrasound and optical imaging). A better estimation of the rotary speed can also help improve the accuracy of determining other effects that are dependent on the speed of the imaging assembly or distal end of the rotary shaft. For example, certain 3D scanning mechanisms implemented on imaging probes can be dependent on the true rotational velocity. Improved estimation of this velocity would be helpful in estimating the scanning pattern of the scanning mechanism, thereby improving the accuracy of reconstruction of 3D imaging data.

Several other devices in minimally invasive procedures would also potentially benefit from the ability to more accurately measure or estimate rotational motion. Such devices would include atherectomy catheters, such as rotational atherectomy catheters, energy delivery catheters (such as those that deliver laser, radioactive, ablative radiofrequency or acoustic energy), and other catheters that inject, cut, palpate, sense or otherwise manipulate tissue in a directed fashion where precise knowledge of the rotational motion of a device component at a remote site would be helpful.

SUMMARY OF RELATED ART

A catheter-based system for intravascular-ultrasound is described by Yock (U.S. Pat. No. 4,794,931) to provide high resolution imaging of structures in blood vessels. This system comprises an outer sheath, within which there is an ultrasound transducer near the distal end of a long torque cable. When a motor rotates the torque cable and ultrasound transducer assembly, 2D cross-sectional images of anatomical structures, such as blood vessels, can be made. Linear translation of the catheter or the torque cable and ultrasound transducer in combination with the rotational motion of the ultrasound transducer allows for acquisition of a series of 2D images along the length of the catheter.

Milo et al (U.S. Pat. No. 5,429,136) and Lenker et al (U.S. Pat. Nos. 6,110,121 and 6,592,526) describe reciprocating and vibrating means for scanning an ultrasound imaging beam in circumferential- or longitudinal directions at the end of the catheter. Reciprocating or vibrating means obviates the need to use a mechanism such as a slip ring to provide an electrical connection to a probe that rotates more than a few rotations in a particular direction, such as more than one or two rotations. Similarly, certain implementations of optical imaging can avoid the use of optical rotary joints using reciprocating or vibrating means.

Liang et al. (U.S. Pat. Nos. 5,606,975 and 5,651,366) describe means of implementing forward-looking intravascular ultrasound where ultrasound is directed towards a mirror with a fixed tilt that causes the ultrasound beam to scan a surface ahead of the probe. The surface scanned approaches the shape of a curved plane, and the resultant shape results from relative rotational motion between the ultrasound transducer and the mirror.

Boppart et al (U.S. Pat. No. 6,485,413) describe several embodiments of optical coherence tomography imaging, including forward looking implementations.

Mao et al (Appl Opt. 2007 Aug. 10; 46(23):5887-94) describe methods for creating ultra-small OCT probes using single mode fiber, coupled to a small length of GRIN fiber which acts as a lens. Including an optical spacer between the fiber and the lens can alter the working distance of the fiber-lens system. Furthermore, a deflecting element can be added to the end of the fiber-lens system by adding a small length of no-clad fiber to the distal end, and cutting the no-clad fiber at an angle. This deflecting element enables side-viewing imaging, which could also be accomplished using a small prism or mirror.

The use of intravascular ultrasound (IVUS) has since become commonplace, with many improvements and adaptations to the technology. A flexible torque cable (Crowley, U.S. Pat. No. 4,951,677) improves the fidelity of the transmission of rotational torque along the length of an IVUS catheter, minimizing non-uniform rotational distortion.

Other approaches that have been considered for minimizing NURD include adding a viscous fluid near the distal end of a rotating conduit (Peterson PCT Application US2003/023019), using an imaging catheter that vibrates across a small range of angles rather than continuous rotation (Lenker U.S. Pat. Nos. 6,110,121 and 6,592,526), using a turbine system (Milner US Application 20070161893 and Feldman PCT Application US2004/012773), image processing algorithms (Sathyanarayana, WO/2003/067526) or putting the rotary drive near the distal end of the catheter to avoid the need for an elongate torque cable (Lancee, U.S. Pat. No. 5,375,602). It is advantageous to consider novel means to of compensating or reducing the effect of NURD when contemplating the implementation of novel imaging systems that involve a torque cable or other rotational element to effect scanning of the imaged tissue.

In chapter 5 of a thesis written by Harm Ten Hoff ("Scanning Mechanisms for Intravascular Ultrasound Imaging: A Flexible Approach" at Erasmus University, Rotterdam, Netherlands, 1993), a general approach of directly measuring the rotational velocity of the distal region of an intravascular imaging catheter is described. The approach uses a light source, a fiber optic transmission line along the drive shaft of the imaging catheter, a rotary encoder near the distal end of the imaging catheter, a beam splitter near the proximal end of the fiber and a light detector. Under Hoffs system, the fiber optic would emit light onto a disc with a reflective pattern encoded upon it that varies the amount of light back-reflected into the fiber as the drive shaft rotates. These variations in back-reflected light would be detected by a detector on a separate segment of the optical circuit coupled to the emitting fiber optic via a beam splitter. The detector output would then be used to detect an incremental change in the angular position of the rotary shaft. The rotary discs tested included those made of nickel foil on a glass ceramic substrate and nickel on silicon substrate.

Methods to pattern the reflective nickel on the substrate included photochemical lift-off, photochemical etch and laser engraving. The fiber optics tested or described by Hoff included single mode and multimode fibers but did not include any lenses or collimators. The implementations described by Hoff primarily consist of those where the fiber optic rotates with the drive shaft while the encoder is stationary. Hoff briefly eludes to a design where the fiber optic is stationary and the encoder rotates, but does not appear to provide technical detail for implementation. All approaches were eventually abandoned at the time due to perceived complexity, mechanical instability, close tolerances required for the design and cost constraints.

Optical coherence tomography (OCT) generally has superior resolution to ultrasound and has the potential to better identify some structures or components in vascular and other tissues. Meanwhile, ultrasound has the ability to better penetrate through biological media such as blood and soft tissues and has a depth of penetration that typically extends several millimeters beyond that of optical coherence tomography. The ability to image with either or both methods of imaging using a combined imaging device provides advantages with respect to selecting the required resolution and depth of penetration. Improvements in estimating or measuring rotational motion along an imaging probe may help enable the accurate co-registration of images when more than imaging modality is used (such as IVUS and OCT).

Angioscopy, endoscopy, bronchoscopy and many other imaging devices have also been described which allow for the visualization of internal conduits and structures (such as vessels, gastrointestinal lumens and the pulmonary system) in mammalian bodies based on the principle of illuminating a region within the body near the distal end of a rigid or flexible shaft. Images are then created by either having a photodetector array (such as a CCD array) near the end of the shaft or by having a bundle of fiber optics transmit the received light from the distal end of the shaft to the proximal end where a photodetector array or other system that allows the operator to generate or look at an image representative of the illuminated region. Fiber bundles are bulky and reduce the flexibility of the shaft among other disadvantages.

Amundson et al describe a system for imaging through blood using infra-red light (U.S. Pat. No. 6,178,346). The range of the electromagnetic spectrum that is used for their imaging system is selected to be one which optimizes penetration through blood, allowing optical imaging through blood similar to that afforded by angioscopy in the visible spectrum, but without the need to flush blood away from the region being imaged.

SUMMARY OF THE INVENTION

The present invention provides means for accurately measuring or estimating the rotational velocity near the distal end of a minimally invasive medical device, such as an imaging probe which undergoes rotational movement to scan surrounding tissue in bodily lumens and cavities.

Embodiments of the present invention provide means for minimizing the effect of non-uniform rotational distortion that occurs in imaging systems that use an elongated rotary shaft.

Embodiments of the present invention improve the ability to co-register imaging data acquired by more than one imaging means incorporated into an imaging probe that has a rotary component.

Embodiments of the present invention to use the estimation of the rotational velocity near the distal end of the imaging probe to provide information that is useful for reconstruction of 3D imaging data when the probe includes a 3D scanning mechanism whose behavior is dependent, at least in part, on the rotational velocity of the distal end of the rotary probe.

Therefore an embodiment of the present invention provides an imaging probe for insertion into bodily lumens or cavities for imaging a vicinity of said bodily lumens or cavities, comprising:

a) an elongate hollow shaft having a longitudinal axis having distal and proximal end sections and an elongate midsection, an imaging assembly being located in said elongate hollow shaft remote from said proximal end section for emitting an energy beam and receiving reflected energy signals reflected back from vicinity of bodily lumens or cavities, said imaging assembly being connected to a first end of an imaging conduit, said imaging conduit extending through the elongate hollow shaft and having a second end, extending through the said proximal end section of said hollow shaft, said imaging conduit being configured to deliver energy to said imaging assembly;

b) rotational drive mechanism for imparting rotational motion to said imaging conduit and said imaging assembly about said longitudinal axis;

c) a scanning mechanism configured to deliver said energy beam along a path out of said elongate hollow shaft to give forward or side viewing capability of said imaging assembly;

e) a rotary encoder mechanism including a light source and an encoder member, said encoder member having an encoder interface located within or upon said encoder member, said encoder interface including features that interact with light, said rotary encoder mechanism including a first encoder fiber optic having a distal end wherein the first encoder fiber optic extends along a portion of said elongate hollow shaft, through which light is emitted towards said encoder member having said encoder interface which interacts with said emitted light, light collection means for collecting light, where said collected light results from the interaction of said emitted light with said encoder interface, detection means for detecting said collected light, said rotary encoder mechanism connectable to an image processing and display system, and wherein as said encoder member experiences rotary motion relative to said distal end of said first encoder fiber optic, light emitted from said distal end of said first encoder fiber optic interacts with said encoder interface and is detected by said detection means, an output of said detection means being used by said image processing and display system to estimate or measure the rotational motion of said imaging mechanism; and e) said rotary encoder mechanism including at least one distal optical element optically coupled to said distal end of said first encoder fiber optic.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

Preferred embodiments of the invention will now be described, by way of example only, with reference to the drawings, in which:

FIG. 2 is a perspective drawing of a flexible imaging probe with an adapter, conduit and imaging assembly;

FIG. 2a is a cross sectional view of the mid section of the imaging probe of FIG. 2 taken along the dotted line;

FIG. 2b is an expanded perspective drawing of the distal region of the imaging probe of FIG. 2;

FIG. 2c shows a schematic of how the rotary and non-rotary components of the imaging probe can be coupled with an adapter to the rest of an imaging system.

FIG. 2d is a perspective drawing of an example of the coupling of the rotary and non-rotary components of the probe to an adapter.

FIG. 3a shows one embodiment of an over-the-wire configuration for an external sheath that may be incorporated with the imaging probe if a guidewire lumen is included;

FIG. 3b shows a cross-section through the imaging probe to demonstrate the guidewire lumen configuration.

FIG. 3c shows a rapid access configuration for an external sheath that may be incorporated with the imaging probe if a guidewire lumen is included;

FIG. 3d shows a cross-section through a portion of the imaging probe that does not contain a guidewire lumen;

FIG. 3e shows a cross-section through a portion of the imaging probe that does contain a guidewire lumen;

FIGS. 4a-4d show schematics for different embodiments of the optical circuit required for most of the optical encoders of the present invention;

FIG. 9 shows the cross-section of an encoder interface constructed to provide information regarding rotary motion as a result of differences in the intensity of light reflected back from an interface, where the differences in intensity result from constructive and destructive interference of light reflected from the interface;

FIG. 10a shows the cross-section of encoder interface constructed to provide information regarding rotary motion as a result of reflection from a variable interference interface;

FIG. 10b shows the cross-section of encoder interface constructed to provide information regarding rotary motion as a result of transmission through a variable interference interface;

FIG. 10c shows a representative plot of the wavelength with peak intensity detected by a photodetector as a result of changes in the intensity of light detected from a variable interference interface during rotational motion;

FIG. 10d shows two annuli that each have different orientations for their respective axes along which the wavelength of detected peak intensity varies;

FIGS. 11a-11b show cross-sections of encoder interfaces constructed to provide information regarding rotary motion as a result of changes in the intensity of light detected from a polarization-based interface;

FIGS. 11c-11f show a progression of movement where the encoder interface rotates around an axis while the distal end of an optical encoding circuit is relatively static;

FIG. 11g shows a representative plot of the intensity of light detected by a photodetector as a result of changes in the intensity of light detected from a polarization-based interface during rotational motion;

FIGS. 11h-11k show a progression of movement where the distal end of an optical encoding circuit rotates around an axis while the encoder interface is relatively static;

FIG. 13b is a side view of the imaging assembly in FIG. 13a;

FIGS. 14a, 14b, 14d and 14e are cross sectional views of elongate medical devices that incorporate embodiments of an optical rotary encoder;

FIG. 14c is a cross-sectional view of the medical device in FIG. 14b through line 14c-14c;

FIG. 16a is a cross-sectional view of an imaging probe that has a reflective tiltable component enabling forward looking imaging; and FIG. 16b is a cross-sectional view of the imaging probe in FIG. 16a through line 16b-16b.

DETAILED DESCRIPTION OF THE INVENTION

Figure 1:
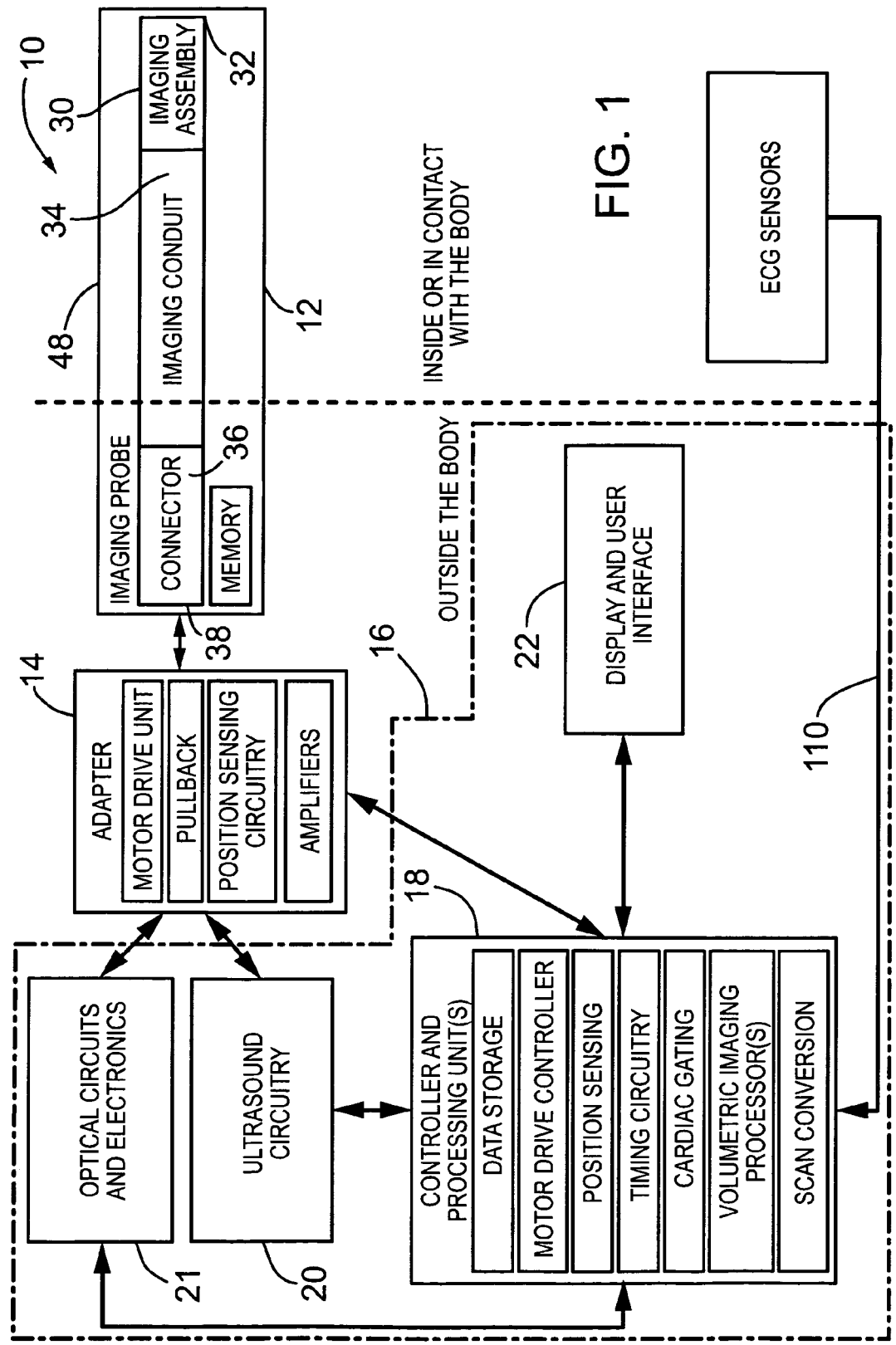
FIG. 1 is a schematic of an imaging system including ultrasound and optical imaging components.

Without limitation, the majority of the systems described herein are directed to an imaging probe using either optical or ultrasonic (or both) imaging. The imaging probe includes means for estimating a rotational motion near the distal end of a rotating shaft within the probe. As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an imaging probe.

As used herein, the term "about", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions of components of an imaging probe are given but it will be understood that these are not meant to be limiting.

As used herein, the phrase "co-registration of images" refers to the process of identifying a subset of imaging data acquired by one imaging means with a subset of imaging data acquired using another imaging means where the identified imaging data from the two means was acquired by detecting a form of imaging energy (e.g. photons or ultrasound) from the same object (or tissue in the case of the present invention).

Each co-registered point in the first subset can then be mapped to a corresponding point in the second subset such that the two points from the two different imaging means are thought to have been acquired from a similar focal region of the imaged object (or tissue).

Successful and accurate co-registration of images, or portions thereof, between images acquired using two (2) or more imaging means is helpful in that it can provide multiple opportunities to assess features of interest of the imaged object by more than one imaging means.

Broadly, the rotary encoder embodiments described in the present invention are capable of providing an estimate or measurement of either the absolute angle of rotation or incremental changes in the angle of rotation of a rotary shaft or a component attached to rotary shaft. Some of the embodiments that provide incremental estimation of rotary motion can also provide an indication of the direction of rotation, although the direction of rotation is often previously known based on the direction of torque applied to the shaft. The site along the rotary shaft at which the estimation or measurement occurs is remote to the site at which the torque is applied. Without limiting the scope of the present invention, the torque is typically applied at a proximal end of a rotary shaft and the site at which the measurement or estimation is made is near a distal end of the shaft. For example, the rotary shaft for an imaging probe for minimally invasive use is mechanically coupled to a motor drive unit that resides outside of the patient.

The rotary motion of the motor drive unit and the proximal end of the rotary shaft can be measured or estimated with fairly good precision—using currently available rotary encoders, such as optical encoders, magnetic encoders, resistive encoders and several others well known in the art. The output of these encoders may be used to provide input to a controller to help control the speed of the motor drive unit and the proximal end of the rotary shaft. However, the loss of ideal transmission of torque along the length of the shaft can result in changes in the rotary motion along the length of the shaft. Typically, the further distally along the rotary shaft, the less closely the rotary motion at that point will match the motion of the proximal end of the shaft.

While several rotary encoders are suitably available for conventional use outside of the body, there are no such encoders readily available for suitable use inside the body. Size constraints are imposed by both the size of anatomical structures and a desire to minimize trauma during delivery and use of the imaging probe. For example, coronary arteries are typically 2-5 mm in diameter and most catheters or devices conventionally inserted into such vessels are between 0.25 to 2.5 mm in diameter.

Other devices into which the encoders could foreseeably be incorporated would include minimally invasive imaging probes, atherectomy devices, steering probes, energy-delivery devices (such as for localized delivery of radiation, radiofrequency ablation, thermal energy, cooling probes, therapeutic ultrasound or light energy) and minimally invasive surgical devices. The majority of these devices are single-use in nature to prevent the likelihood of transmission of infectious diseases and to ensure reliable product performance. Single-use devices have more significant limitations in terms of the cost at which they can be made compared to reusable devices or probes.

FIG. 1 represents an overview of an exemplary imaging system constructed in accordance with the present invention shown generally at 10. It comprises an imaging probe 12, which connects via an adapter 14 to an image processing and display system 16. The image processing and display system 16 comprises the necessary hardware to support one or more of the following imaging modalities: 1) ultrasound, 2) optical coherence tomography, 3) angioscopy, 4) infrared imaging, 5) near infrared imaging, 6) Raman spectroscopy-based imaging and 7) fluorescence imaging.

Implementations of the optical coherence tomography, ultrasound, angioscopy and infrared imaging circuitry have been described in the prior art.

The system herein described further typically comprises a controller and processing unit 18 to facilitate the coordinated activity of the many functional units of the system, and may further comprise a display and/or user interface and may further comprise electrode sensors to acquire electrocardiogram signals from the body of the patient being imaged. The electrocardiogram signals may be used to time the acquisition of imaging data in situations where cardiac motion may have an impact on image quality. The optical circuits and electronics 21 forming image processing and display system, if included in a particular implementation of the present invention, may include any or all of the following components: interferometer components, one or more optical reference arms, optical multiplexors, optical demultiplexors, light sources, photodetectors, spectrometers, polarization filters, polarization controllers, timing circuitry, analog to digital converters and other components known to facilitate any of the optical imaging techniques described in the background and prior art sections. The ultrasound circuitry 20 may include any or all of the following components: pulse generators, electronic filters, analog to digital converters, parallel processing arrays, envelope detection, amplifiers including time gain compensation amplifiers and other components known to facilitate any of the acoustic imaging techniques described in the background and prior art sections.

The controller and processing units 18, if included in a particular implementation of the present invention, serve multiple purposes and the components would be markedly adapted based on the needs of a particular imaging system. It could include one or a combination of motor drive controller, data storage components (such as memory, hard drives, removable storage devices, readers and recorders for portable storage media such as CDs and DVDs), position sensing circuitry, timing circuitry, cardiac gating functionality, volumetric imaging processors, scan converters and others. A display and user interface 22 is also optionally provided for either real time display or display of data at a time later than the time at which imaging data is acquired.

The imaging probe 12 comprises an imaging assembly 30 near its distal end 32, an optional conduit 34 along a substantial portion of its length, and a connector 36 at its proximal end 38. For the purposes of this invention, an imaging assembly 30 generally refers to the component of the imaging probe 12 from which the signals (acoustic or optical (or both)) are collected for the purposes of imaging a region that is proximate to the imaging assembly 30. The imaging assembly 30 includes at least one or more emitters of imaging energy and at least one or more receivers of imaging energy. For the purposes of this invention, "imaging energy" refers to both light and acoustic energy. Specifically, light refers to electromagnetic waves that span the ultraviolet, visible and infrared spectrum of wavelengths. For example, for acoustic imaging, the imaging assembly 30 contains an ultrasound transducer that is both an emitter and receiver of acoustic energy.

For optical imaging, the imaging assembly 30 typically contains the distal tip of a fiber optic, as well as a combination of optical components such as a lens (such as a ball lens or GRIN lens), which collectively serve the purpose of acting as an optical receiver and may also serve as an optical emitter. A mirror and/or a prism are often incorporated as part of an optical emitter and/or receiver. The imaging assembly 30, connector 36 and/or imaging conduit 34 may be liquid-filled, such as with saline and may be flushed.

The imaging probe 12 may contain ports at one or more points along its length to facilitate flushing. For optical imaging, it is possible to consider a gas filled imaging probe 12. Preferably, the gas would substantially comprise carbon dioxide or another readily dissolved gas. Alternatively, the imaging assembly may be compartmentalized such that there is at least one gas-filled compartment or lumen for optical imaging and at least one fluid-filled compartment or chamber for acoustic imaging.

The imaging conduit 34 comprises at least one optical waveguide and at least one conductive wire (preferably two or more) that connect an emitter and/or receiver via a connector to an adapter. The imaging conduit 34 may also act as a mechanical force transmission mechanism for rotating or translating the imaging assembly. For example, the imaging conduit 34 may comprise a fiber optic, wrapped by two layers of electrical wire that are insulated by each other. The imaging conduit 34 may further be reinforced by other structural features, such as helically wrapped wires or other designs used to construct imaging torque cables for rotating scan mechanisms, as described in the prior art.

The adapter 14 facilitates transmission of signals within any fibers and/or wires to the appropriate image processing units. The adapter 14 may also incorporate a pullback mechanism 49 (FIG. 2d) or a reciprocating push-pull mechanism to facilitate longitudinal translation of the imaging assembly. Such longitudinal translation of the imaging assembly 30 may occur in conjunction with the longitudinal translation of an external shaft that surrounds the imaging conduit 34, or may occur within a relatively stationary external shaft.

Additional sensors may be incorporated as part of the adapter 14, such as position sensing circuitry, for example to sense the angle of rotation of a rotary component within the imaging probe 12. The imaging probe 12 may also include a memory component such as an EEPROM or other programmable memory device that includes information regarding the imaging probe to the rest of the imaging system. For example, it may include specifications regarding the identification of specifications of the imaging probe 12 and may also include calibration information regarding the probe 12.

While precise alignment of the acoustic and optical imaging data is highly desired, it is also important to recognize the need to optimize the geometry of a minimally invasive probe so that it is as small as reasonably possible to achieve its desired purpose. Current IVUS probes are approximately 0.9 to 2 mm in diameter and the smaller sizes of probes can be delivered more distally within the vascular tree of the coronary anatomy as the vessel size tapers down. Thus, smaller sizes generally allow for interrogation of a larger portion of the coronary anatomy. It is therefore desirable to have embodiments of a probe that combines optical and acoustic imaging in arrangements that minimize certain dimensions of the probe, such as the diameter of the probe.

FIG. 2 is a perspective drawing of a flexible catheter containing a fiber optic 40 and a co-axial electrical wire 50. The proximal connector contains fiber optic 40 that can be received by the adapter to optically couple the imaging fiber optic 40 to the optical imaging system "back-end". There are also electrical connectors 56 that allow the one or more electrical conduits to be connected to the ultrasound circuitry and/or controller and processing units. In embodiments where the imaging conduit rotates around its longitudinal axis, there may be a need to couple the rotating components of the imaging fiber optic with the relatively stationary fiber optic that connects to the optical imaging system's back-end 16. The coupling of a rotating fiber optic probe can be accomplished using a fiber optic rotary joint incorporated either as part of the proximal connector 36 of the imaging probe 10 or as part of the adapter 14. Similarly, in embodiments where the imaging conduit rotates around its longitudinal axis, there may be a need to couple the conductive wires that rotate with the imaging conduit with the relatively stationary conductors of the ultrasound circuitry and/or controller and processing units, preferably by means of slip rings. These slip rings can be incorporated as part of the proximal connector of the imaging probe 36 or as part of the adapter 14.

FIG. 2a shows a cross sectional view of the mid section of the imaging probe of FIG. 2 taken along the dotted line which shows a fiber optic 40, guidewire port 44 and guide wire 42, imaging conduit 34, imaging conduit lumen 46, external sheath 48 which is a hollow, flexible elongate shaft made of a physiologically compatible material and having a diameter suitable to permit insertion of the hollow elongate shaft into bodily lumens and cavities, and coaxial electrical wiring 50. The expanded detailed view of the end of the imaging probe 10 shown in FIG. 2b shows the distal end of the guidewire 42 extended beyond the end of the outer sheath 48 and a flush port 54 at the end of the sheath 48. In FIG. 2 the proximal end of the imaging probe 10 includes another guidewire port 55 into which guidewire 42 is inserted and the connector assembly 36 which includes a flush port 58 and electrical contacts 56 along the connector body.

FIG. 2c shows a schematic of how the rotary and non-rotary components of the imaging probe can be coupled with an adapter to the rest of an imaging system. FIG. 2d schematically shows how the rotating components of the imaging probe can be coupled to the rotating components of an adapter. The rotating components of each can be electrically, optically and/or mechanically coupled using connectors and other configurations known in the art. Similarly, the non-rotating components of the imaging probe can be coupled to the non-rotating components of the adapter 14. The adapter 14 can include slip rings, optical rotary joints and other such implements for electrically or optically coupling a rotary component to a non-rotary component and enable communication of necessary electrical and optical signals with the rest of the system.

Dual-fiber optical rotary joints are also available but considerably more complex. Electrical coupling between any conductor mounted onto a rotating component in the imaging probe 12 can be coupled to non-rotating conducting elements via metallic slip rings and springs, metallic slip rings and brushes or other commonly known methods of forming conductive contact between a stationary conductor and a rotary conductor.

While the electrical, optical and mechanical connections are shown separately in FIG. 2d, it is possible to reduce the several connectors that must each be separately connected between the probe and adapter with fewer connectors by combining several connectors into combined connectors, as needed for a specific embodiment.

Figure 3A:
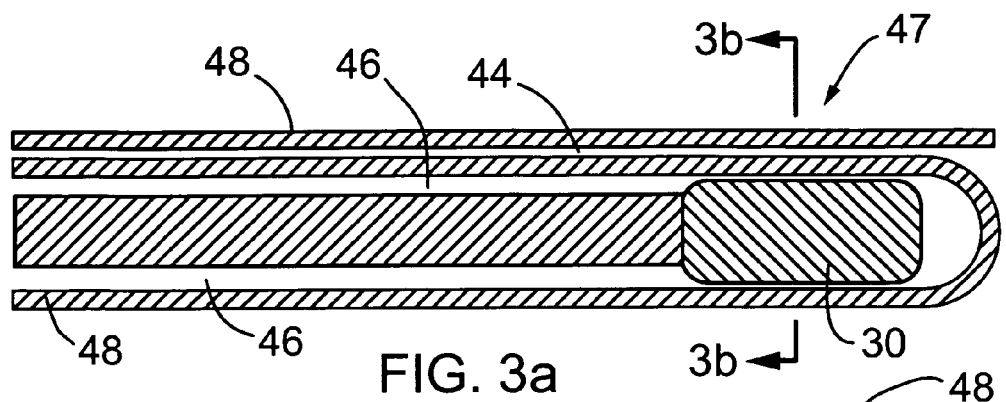
FIGS. 3a to 3e are representative of general imaging catheter configurations described in the literature.
Figure 3B:
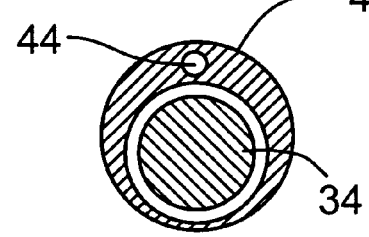

FIG. 3a shows one embodiment of an over-the-wire configuration for an external-sheath at 47 and FIG. 3b shows a cross-section of sheath 47 through the portion that contains the imaging assembly 30 along the vertical line 3b-3b in FIG. 3a.

Figure 3C:
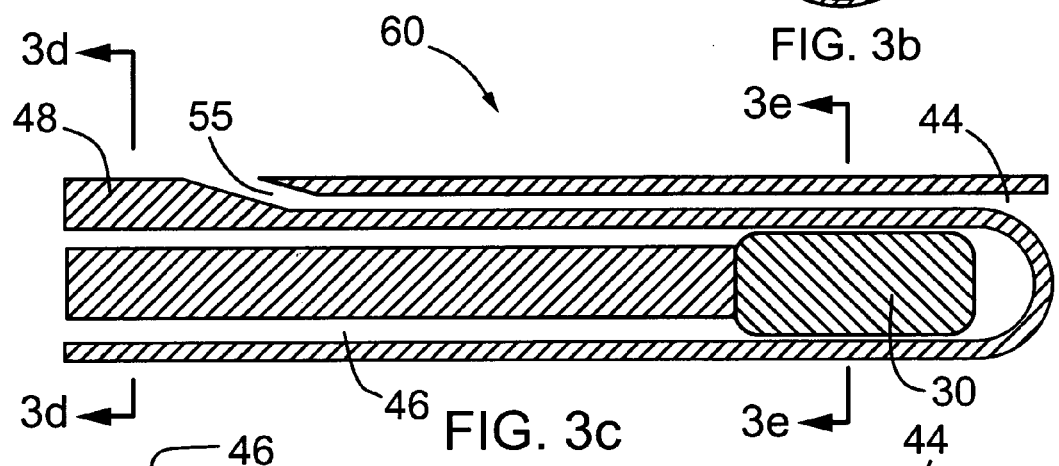
Figure 3D:
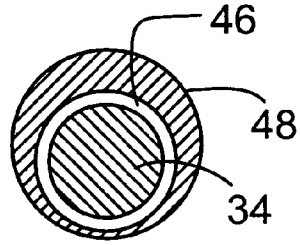
Figure 3E:
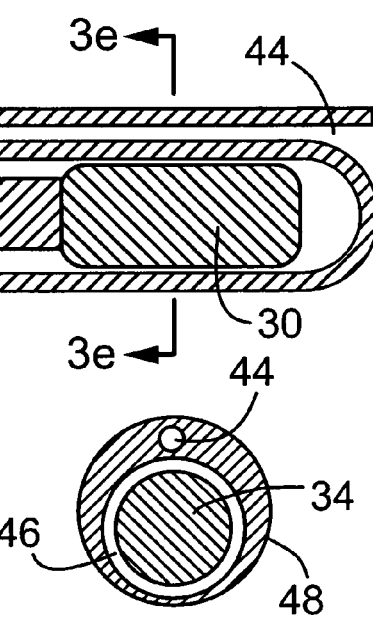

FIG. 3c shows an embodiment at 49 that is a "rapid exchange" configuration for the external sheath that may be incorporated with the imaging probe if a guidewire is required. Sheath 49 in FIG. 3c includes the entry port 55 shown in FIG. 2. FIG. 3d shows a cross-section of the "rapid-exchange" configuration 49 through the portion that is proximal to the entry port 55 for a guidewire along line 3.d-3d in FIG. 3c. FIG. 3e shows a cross-section along line 3e-3e in FIG. 3c.

FIG. 4a shows a schematic of an embodiment of an optical rotary encoder circuit 100 that may be incorporated into an imaging probe or other medical device discussed hereinafter. Light is generated by a light source 122 and is coupled into a first fiber optic segment 114. The coupling can occur by positioning and orienting the proximal end of the first fiber optic segment adjacent to the light source. The coupling of light into fiber optics is well known in the art and may optionally involve the use of a lens 120, collimator or other optical components useful for coupling light into optical fibers. The light source may be any light source known in the art, such as a laser, LED, bulb or other such component. Light propagates along the first segment 111 of the fiber optic towards an optical coupling component 112, such as a beam splitter, fiber coupler or circulator for example. Light then travels along a second fiber optic segment 113 that substantially resides along the length of the imaging probe to a position proximate to where the rotational velocity of the rotary component is to be estimated or measured. The second fiber optic segment 113 may include an optional optical rotary joint 114 if the imaging probe design requires such a joint to minimize torque within the encoder circuit.

Light from the second fiber optic segment 113 then propagates through some optical-components at its distal end before propagating towards an encoder interface. The distal optical components 115 may include any of the following, including one or more lenses, collimators, mirrors, prisms, optical spacers or polarizers. The light emitted from the distal optics then interacts with the encoder. The possible interactions of the encoder with the emitted light are several and will be described later on. As a result of the interaction between the emitted light and the encoder, some light will then return back towards the distal optics 115 during one or more time periods throughout the rotation of the imaging probe. All or a portion of this light will be coupled back into the second segment 113 of the fiber optic and will return towards the proximal end of the encoder circuit. The returning light will travel through the optical coupling component 112, some of which will be directed towards a photodetector 118 via a third segment 116 of fiber optic. The output of the photodetector 118 will then be used to estimate or measure the rotational motion.

It should be noted that the inclusion of the optional rotary joint is shown in the second fiber optic segment 113 of the embodiment in FIG. 4a, but could alternatively be included in either the first 111 or third 116 segments of fiber optic. In those embodiments where the rotary joint 114 is in the first segment 111, the photodetector 118, third segment 116 of fiber optic and the coupling mechanism 112 (splitter, coupler or circulator) would be rotary components of the adapter 14 and imaging probe 12. In those embodiments where the rotary joint 114 is in the third segment 116, the light source 122, first segment of fiber optic 111, proximal optics 120 and the coupling mechanism 112 would be rotary components of the adapter and imaging probe. It should be noted that in many embodiments, the optional rotary joint may be completely omitted.

FIG. 4b demonstrates a schematic for an alternative optical encoder circuit 120 whereby the light from the light source 122 towards the encoder interface 104 is carried on a separate optical fiber 117 than the light that returns from the encoder interface 104 to the photodetector 126. This modification makes it possible to avoid the need for the optical coupling mechanism 112 (e.g. beam splitter, fiber coupler or circulator) shown in FIG. 4a. The light source 122 is optically coupled to an emitting fiber 117, possibly through some proximal optics 120. The emitted light then travels through some optional distal emission optics 130 and interacts with the encoder interface 104. Based on the interaction of the emitted light with the encoder interface 104, some light will, during at least one or more periods during a rotation of the probe, return towards the detection fiber 121 via some optional distal detection optics 131.

Light coupled into the detection fiber 121 will then be transmitted to a photodetector 126 for further analysis. In the case of the embodiment of FIG. 4b, either the distal emitting optics 130 or the distal detection optics will typically comprise one or more lenses, collimators, mirrors, prisms or polarizers.

Figure 4C:
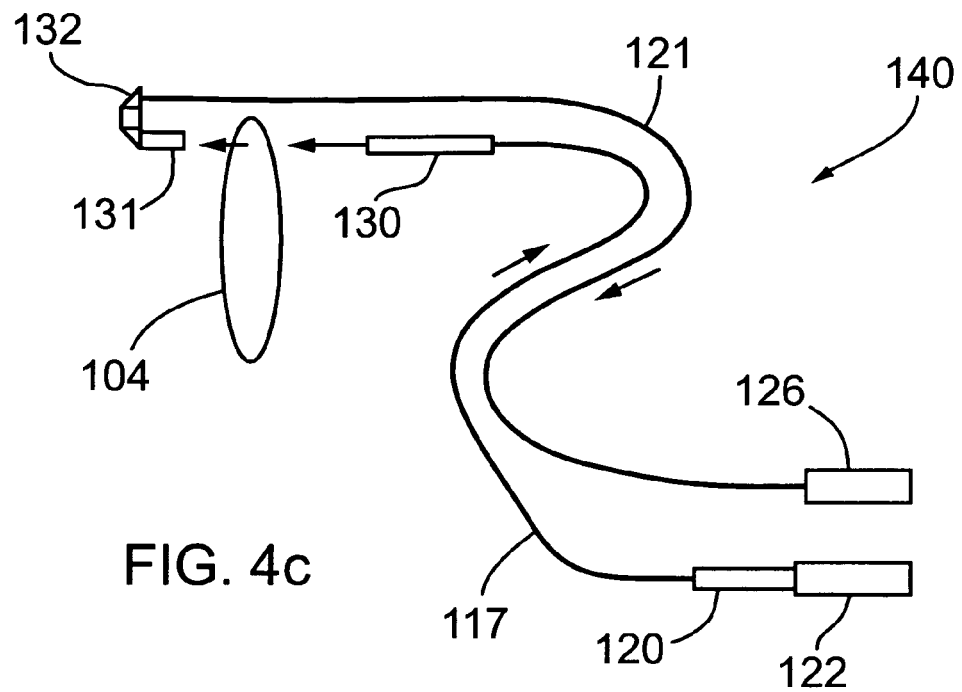

FIG. 4c shows the schematic of another embodiment of an encoder circuit 140 where the light emitted from the emitting portion of the circuit interacts with an encoder interface 104. In this embodiment, the encoder interface is interposed between the distal end of the emission portion of the circuit and the detection portion of the circuit. This is most relevant for creating a miniaturized encoder that changes the amount and/or properties of transmitted light through the encoder. Either the emitting optics 130 or the detection optics 131, may comprise a series of deflection components 132 such as prisms or mirrors to help deflect light in a tight radius that cannot be reliably or conveniently achieved with an optical fiber.

Figure 4D:
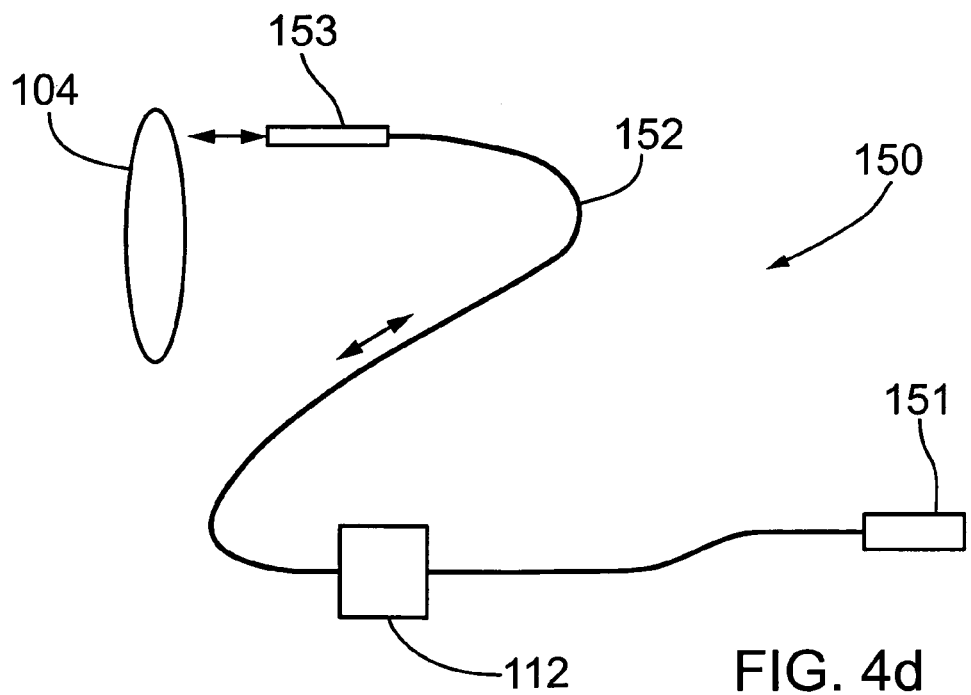

FIG. 4d shows the schematic of another embodiment of an OCT-based encoder circuit 150 where an OCT-based detection system 151 known in the art, such as an OCT-based imaging system (without the usual imaging fiber), replaces the light source 122 and detector 126. The OCT-based detection system is connected to an OCT detection fiber 152 that may be interrupted by an optical rotary joint. Distal optics 153 at the end of the OCT-based detection fiber are similar to those use for OCT imaging fibers, such as an optional optical spacer, a lens such as a GRIN lens and an optional deflector, such as a mirror or prism.

There are several properties of light and several interactions in between light and an encoder interface that can be used to help detect rotary motion. Properties of light that can be readily detected include the amplitude, polarization state and the wavelengths comprising an optical signal. The light used for detection can interact with the encoder interface by means of reflection, transmission, attenuation or fluorescence. The reflection, transmission and/or attenuation of light can be further affected by coatings or surface features that cause constructive and/or destructive interference, polarization state dependent attenuation or scattering.

Figure 5A:
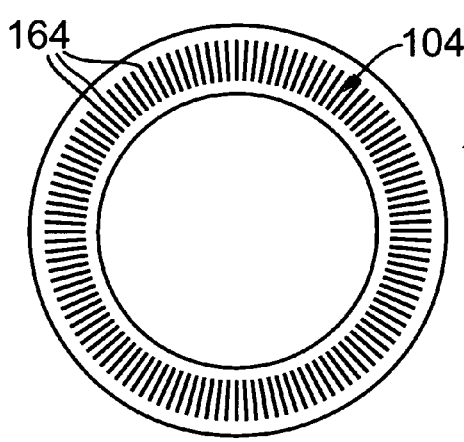
FIGS. 5a-5e show different bodies of encoder interfaces that could be applied towards the current invention for the various embodiments of the present invention.
Figure 5B:
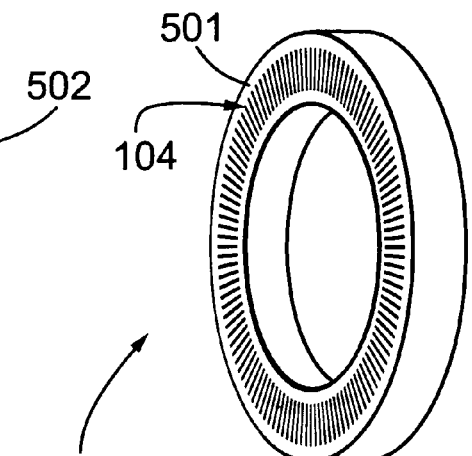

For the purposes of implementing a rotary encoder, light can be emitted in any of several directions onto the encoder. FIGS. 5a and 5b show an annular-shaped body with an encoder interface 104 on a generally flat surface 501 of the encoder interface body 502. The particular encoder interface 104 seen in FIGS. 5a and 5b depicts a series of radially oriented lines 164 on a generally flat surface 501 of the encoder interface body 502. As will become evident below, the encoder interface 104 need not be on a flat surface 501, but can also be on a beveled or rounded surface without loss of functionality. The encoder interface 104 is shown as a series of lines, but can be embodied using several different encoding principles that will be described herein.

Figure 5C:
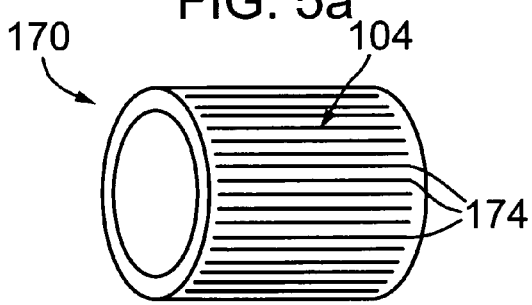
Figure 5D:
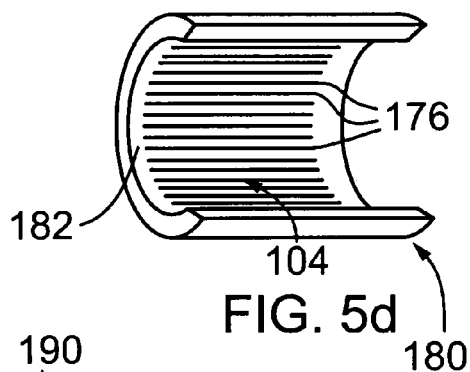
Figure 5E:
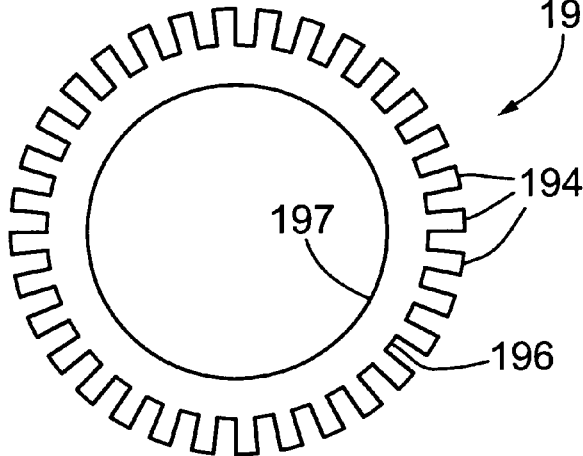

FIG. 5c shows an encoder interface 104 on the outer surface of a cylindrical encoder interface body 170. The particular pattern shown in FIG. 5c comprises a series of lines 174 oriented along the longitudinal axis of the cylinder 170. FIG. 5d shows a part of a cylindrical encoder interface body 180 whereby the encoder interface 104 is on the inner surface 182 of a cylinder. The particular pattern shown in FIG. 5d comprises a series of lines 176 oriented along the longitudinal axis of the cylinder 182. FIG. 5e shows an alternative embodiment of an encoder interface body 190 comprised of radially projecting fingers 194 around the outer periphery 196 of the encoder interface body 190. An alternative embodiment where the radially projecting fingers 194 project from the inner periphery 197 is also possible.

Figure 6A:
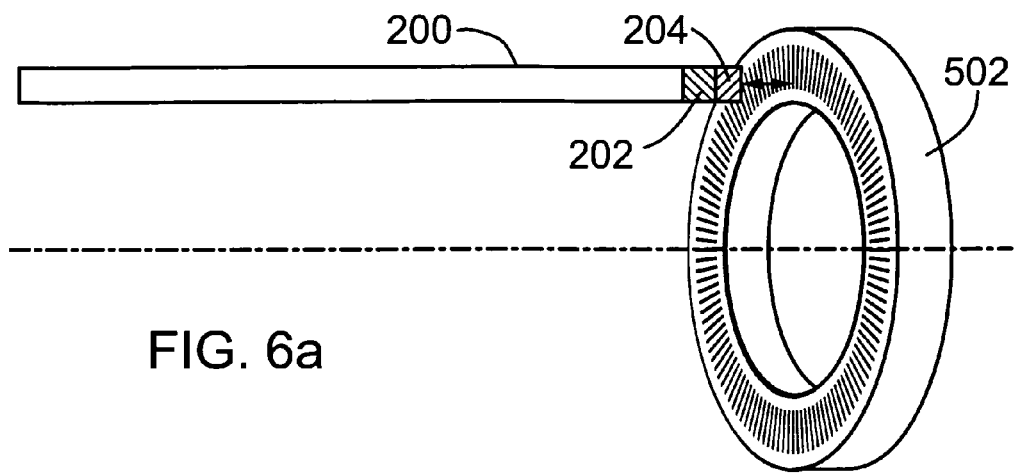
FIGS. 6a-6c show different orientations in which the optical circuit of an encoder can be aligned with an encoder interface.

FIG. 6a shows a fiber optic 200 attached to a spacer 202 and a gradient index (GRIN) lens 204 where focused light is emitted from the fiber optic 200 onto the encoder 160 where the encoder interface 104 on the flat surface 501 of encoder interface body 502 is substantially normal to the longitudinal axis 210 of the probe (dotted line). The fiber optic 200 can be either a; single mode fiber or a multimode fiber and can be selected for the wavelength or range of wavelengths that need to be transmitted for proper functioning of the device. For example, the fiber 200 can be a single mode fiber optic with a cladding whose outer diameter is on the order of 125 microns, ranging from 50 microns to several millimeters.

Distal optics 115 can be added to the distal end of fiber 200. For example, the optical spacer 202 comprising a substantially transparent glass or polymer can be attached to the distal end of the fiber 200. The optical coupling in between the fiber 200 and the spacer 202 can be made by means known in the art, such as via bonding with an adhesive, such as an ultraviolet cured optical adhesive, or by using a fiber fusion splicer which uses an electric discharge to weld the two components together. The GRIN lens 204 (or a ball lens) can be added to the distal end of the optical spacer 202 using similar means. The optical spacer 202 is not required and may simply be used to reduce the precision required for assembly. The methods for OCT probe construction described by Mao (Mao et al (Appl Opt. 2007 Aug. 10; 46(23):5887-94)) discussed in the present Background, can equally be applied for assembling the distal optics 115, including the distal emitting optics 130 and the distal detecting optics 131 described in the present invention. An encoding interface body 190 similar to the one seen in FIG. 5e with the encoding interface at the outer radius of the ring could be substituted for the encoder interface body 502 shown in FIG. 6a for many embodiments.

Figure 6B:
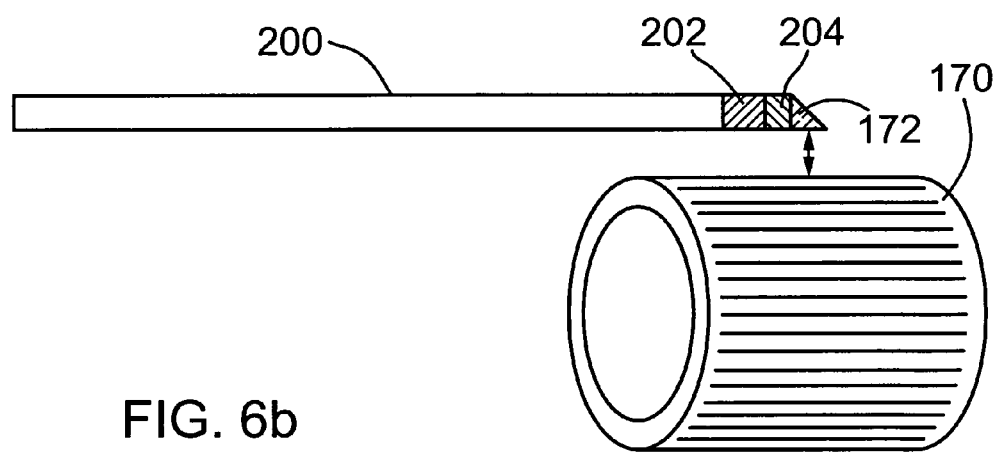

FIG. 6b shows an embodiment of encoder interface body 170 where the emitting fiber 200, spacer 202 and lens 204 are followed by a prism or mirror 172 to deflect light from the fiber 200 (which is generally oriented parallel to the longitudinal axis of the probe) towards the outer surface of the encoder interface body 170. The mirror or prism 172 can be added to the distal end of the lens 204 using methods well known in the art including bonding or welding. Similarly, the method described by Mao for adding a deflector to the end of an OCT probe can be used here. For example, a piece of no-clad fiber can be attached to the lens 204, and then be further cut or polished at an angle, and further still be coated with a reflective coating. In general, the encoder interface body 170 can rotate in conjunction with the rotating components of the imaging probe while the emitting and receiving components of the optical circuit remain relatively static. Alternatively, the emitting and receiving components of the optical circuit can rotate in conjunction with rotating components of the imaging probe while the encoder remains relatively static. Alternatively, in the case where the transmission and detection arms are separate fibers near the distal end, at least one of them rotates relative to the encoder.

Figure 6C:
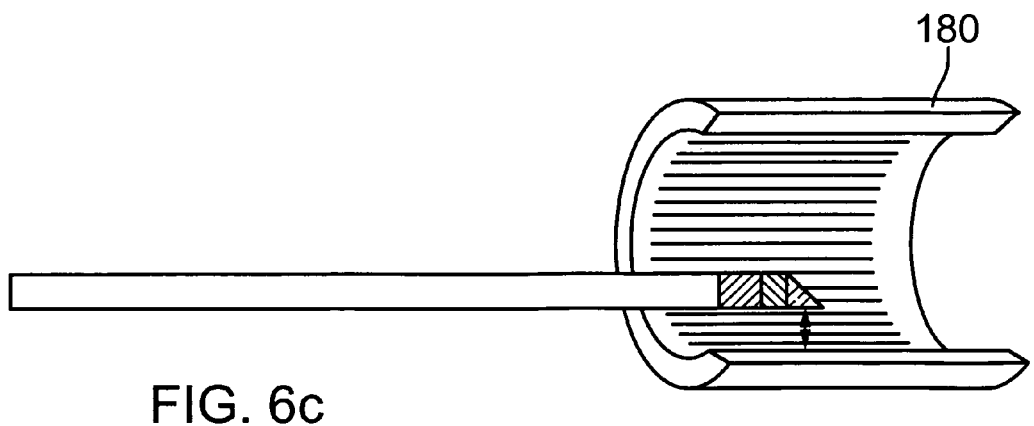

FIG. 6c shows an alternative configuration of the fiber optic and encoder relative to FIG. 6b in which the fiber 200 with attached GRIN lens 202, spacer 204 and prism or mirror 172 are located within encoder interface body 180 of FIG. 5d.

Embodiments of the Encoding Interface

Several different interactions can occur between the light from the optical circuit and the encoder before light returns to the optical circuit. A key principle is that a significant change in the rotary position of the encoder interface relative to the distal end of the optical circuit will cause a change in the properties of the light that returns to the optical circuit for detection.

Transmission or Reflection Based Embodiments

One such interaction is that the interface of the encoder is such that some parts of the encoder reflect light more strongly than others. For example, the radial lines 164 in FIG. 5a could reflect light more strongly or weakly than the portions that are not covered with a line. If the lines are evenly spaced around the center of the encoder, than each line represents a constant angle of revolution. Therefore, as the probe undergoes rotary motion, the amplitude of the light detected by the detector at the proximal end will oscillate between extreme values. Each peak or trough in the detector output will represent an incremental angle of rotation. For example, if an encoding pattern comprises 120 reflective lines on top of a relatively attenuating substrate then there will be a reflective line at each 3 degrees of rotation. Therefore, each peak detected by the photodetector would correspond to 3 degrees of rotation from the previous peak, assuming the probe continues to rotate in the same direction. If we further assume that the light focused upon the encoder by the emitting arm of the circuit is offset at 0.75 mm from the center of rotation, then the arc length between the leading edge of two adjacent lines would be just over 39 microns. While the encoder described by Hoff used unfocused light, the addition of focusing elements to the emitter circuit greatly improves the spatial resolution and relax some of the construction requirements to make this embodiment more feasible. For example, Hoff's description mentions that a single mode fiber implementation without focusing elements should have its distal end positioned with 45 microns of the encoder disc. With a focusing element, the distance in between the distal end of the emitting circuit and the encoder can be considerably longer (several millimeters if needed) but will typically be less than 1-2 mm, while still maintaining an acceptable spot size.

Figure 7A:
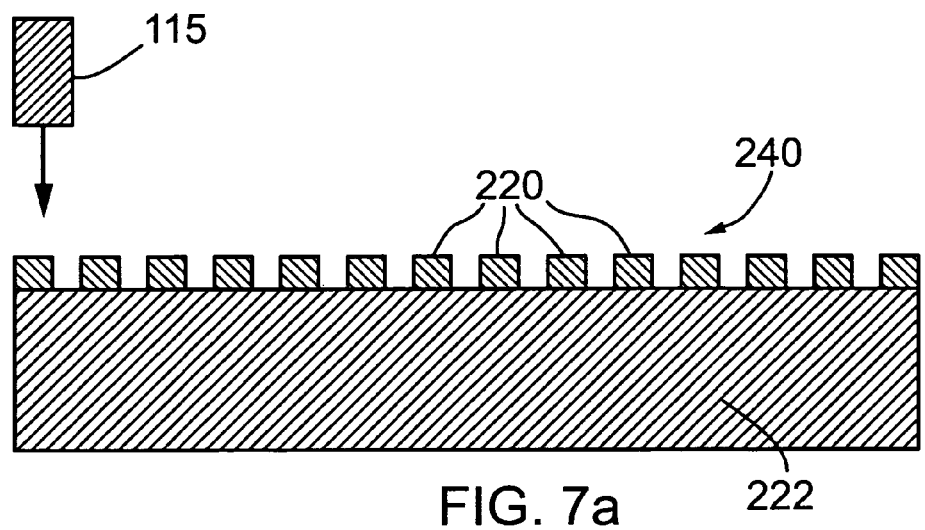
FIGS. 7a-7b, 7d and 7f show the cross-section of encoder interfaces constructed to provide information regarding rotary motion as a result of differences in the intensity of light reflected back from an interface.

FIG. 7a shows a cross-section of a reflection-based encoder interface 240 comprising a pattern of encoder lines 220 that would be used to create an encoding interface 104 on an encoder interface body that would be detectable by the photodetector 126 of an encoder system. The pattern 220 is produced onto a substrate 222 where the pattern has a different amount of reflectivity than the substrate. In the case shown, the pattern 220 is more reflective than the substrate 222, although the opposite could be true based on material selection and processing. As light from the distal optics 115 scans across the encoder interface 240, the amount of light detected being reflected back from the encoder interface 240 will vary and provide a means for measuring the amount of rotation that occurs over time.

The pattern 220 may be produced using several methods, such as chemical etching, laser ablation, laser marking, precision sawing (such as using a dicing saw), precision machining (such as using a computerized numeric control mill with an air spindle and precision grinding bit or precision milling bit), electrical discharge machining and others known in the art. A mold formed using one of these high-precision manufacturing techniques could also be used to create the encoder interface. Reflective materials suitable for such manufacture include metals, such as gold, silver, stainless steel, platinum, chrome, aluminum, but can also include polymers and ceramics that can be doped with reflective dyes, such as white pigment.

Alternatively, thin films of polymer or glass whose thickness is constructed to be of an appropriate thickness in relation to the average wavelength of the incident light (such as an odd number of half wavelengths) would produce a reflective coating. In some cases, to produce a thin layer of the reflective material, it may be helpful to sputter, evaporate or electrochemically deposit a metal or polymer onto another substrate. Less reflective materials include any number of polymers or ceramics, crystalline structures (such as silicon) that can be made less reflective through appropriate choices of material selection, including dyes, pigments, surface treatments (such as oxidation).

For example encoder interfaces have been produced whereby a thin sheet of dark mylar was ablated through the entire thickness using a highly focused excimer laser to create a series of lines. The lines were 50 microns wide and 50 microns apart from each other (i.e. on line every 100 microns). The mylar encoding pattern was placed on a reflective surface and an optical detection circuit similar to that seen in FIG. 4a was used. As the encoder interface was displaced laterally relative to the distal end of the optical detection circuit, the output of the encoder varied with a peak for every 100 microns of displacement and a trough for every 100 microns.

Figure 7B:
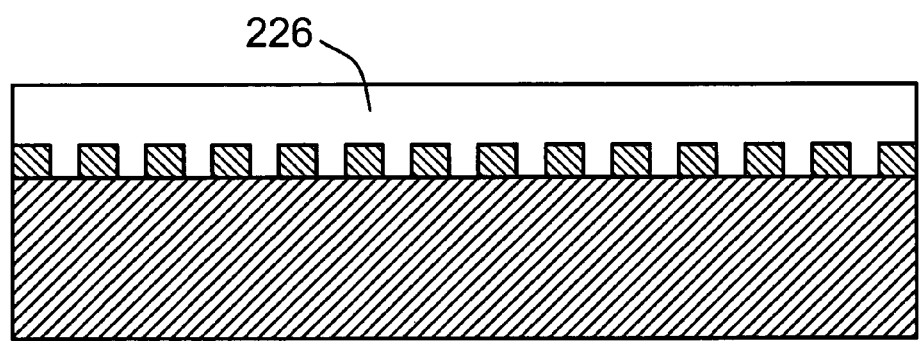
Figure 7C:
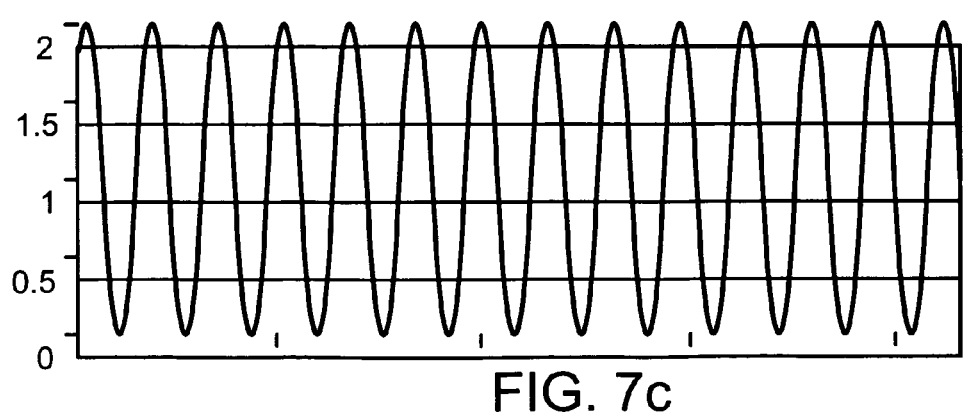
FIGS. 7c and 7e show representative plots of the intensity of light detected by a photodetector as a result of changes in the intensity of light reflected back from an interface during rotational motion.

FIG. 7c depicts an approximation of the output of the photodetector with the output on the Y axis and the displacement on the X-axis. Higher frequency light sources or more tightly focused optics or the use of a collimator or any combination thereof would potentially be able to improve the functional angular resolution of the encoder.

In order to produce a generally radial encoder, such as that seen on encoder interface body 502 in FIG. 5a, the encoder interface 240 seen in FIG. 7a would be such that the pattern of encoder lines 220 comprises radial lines such as the series of radial lines 164 on the flat surface 501 of the encoder interface body 502 seen in FIG. 5a. The reflection-based encoder pattern 220 can be made separate on a generally planar substrate and then attached to a suitable surface on the imaging probe, or could be directly manufactured onto a component of the imaging probe. A generally cylindrical encoder interface, such as those seen on cylindrical encoder interface bodies 170 and 180 in FIGS. 5c and 5d could be produced by either making the encoder pattern 220 on a planar substrate and then wrapping the substrate around an approximately cylindrical surface near the distal end of the imaging probe or by directly producing the encoding pattern 220 on a suitable component of the imaging probe.

Therefore, a separate encoder interface body is not always necessary as separate component of the imaging probe. For example, the shell of an imaging assembly 30 or the distal end of an imaging conduit 34 may have a surface or component that would adequately serve the functional purpose of being an encoder interface body for an encoder interface of the present invention.

Given the potentially delicate nature of the encoding pattern 220, it may be desirable to place a mechanically protective layer over the encoding pattern. FIG. 7b demonstrates the same general concept of a reflectance based encoding interface, whereby the encoder pattern 220 is subsequently covered by an optically transparent coating or layer 226 for protection against damage. The material 226 could be any of a number of substances that do not significantly attenuate the light used for detection, such as polycarbonate, acrylic, polymethylmethacrylate, high density polyethylene and many others. The use of a mechanically protective covering that does not significantly interfere with the encoding mechanism can be extended to all embodiments of encoder interfaces in the present invention.

Figure 7D:
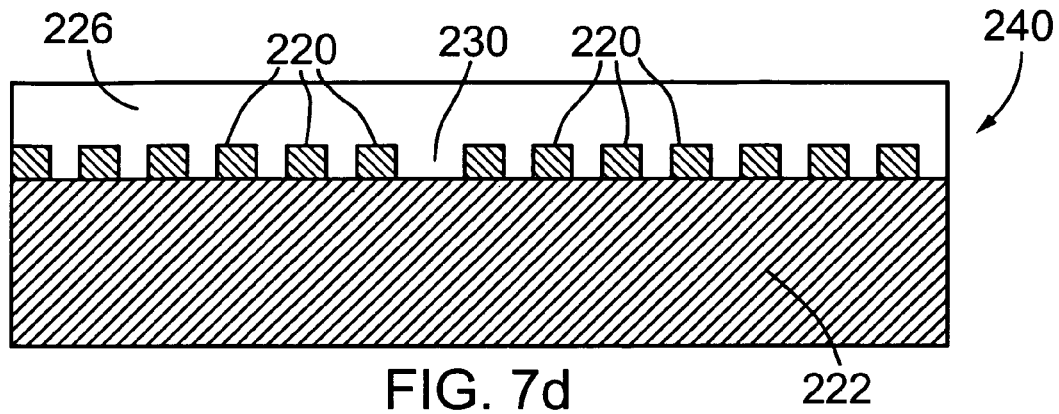
Figure 7E:
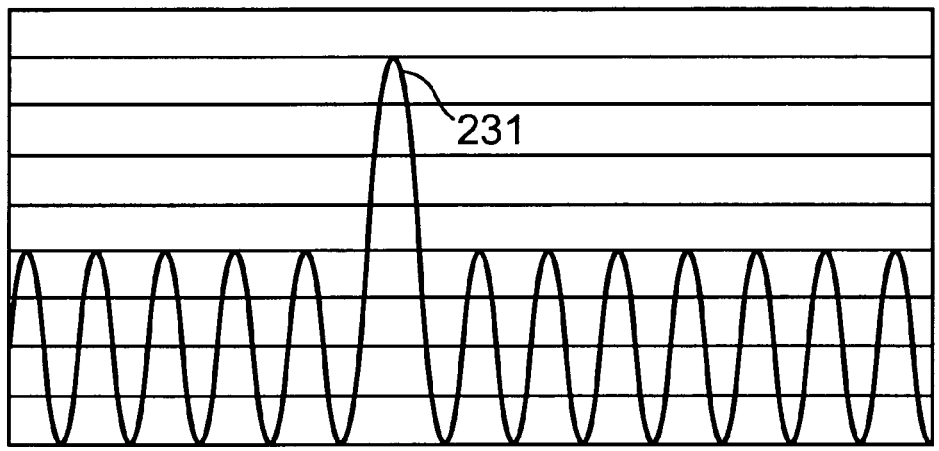

It may be desirable to have the encoder pattern produce a different output for a finite number of occasions each rotation, such as once each rotation in order to provide an index that will assist with either error detection caused by a defect in the encoder or to help measure the absolute angle of rotation relative to a known orientation. The encoder pattern 220 can be intentionally constructed to either make a substantially stronger or weaker reflection at the index positions, to change the center wavelength of the returned light at the index position or to predictably change the spacing between lines or other features in the encoder pattern. Software or hardware that interprets the output of the encoder system's photodetector can then algorithmically recognize these changes in the detector output to determine when an index position has been passed. FIG. 7d shows a larger gap 230 in between two of the encoding lines 220 which would produce, in the case of a reflective substrate and absorptive encoding pattern, a higher peak output 231 from the photodetector 126 at the index position, as seen in FIG. 7e.

Figure 7F:
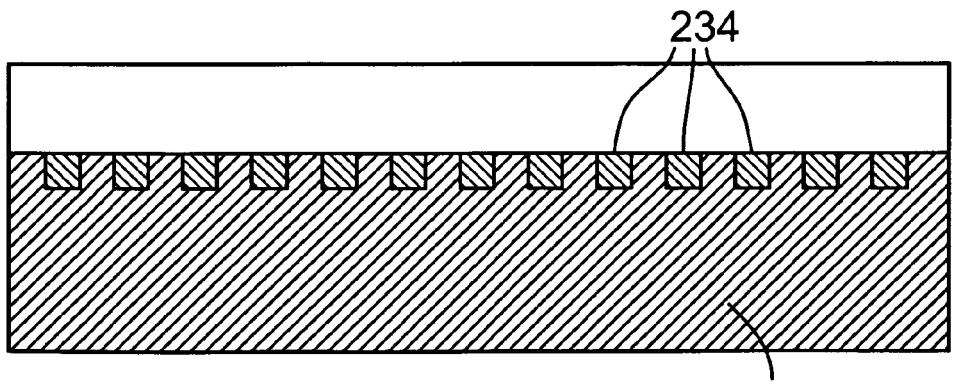

While the encoder pattern 220 can be added onto the top surface of the substrate as seen in FIGS. 7a, 7b and 7d, it can also be recessed as a pattern of recessed features 234 into the substrate 222, as seen in FIG. 7f.

Figure 8A:
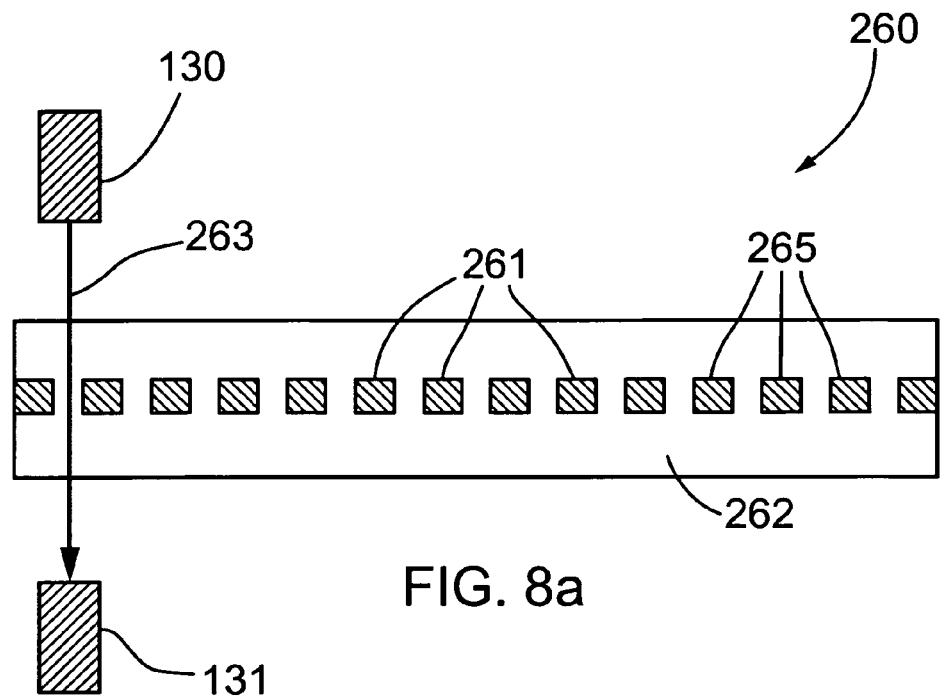
FIGS. 8a-8b show the cross-section of encoder interfaces constructed to provide information regarding rotary motion as a result of differences in the intensity of light transmitted through an interface.
Figure 8B:
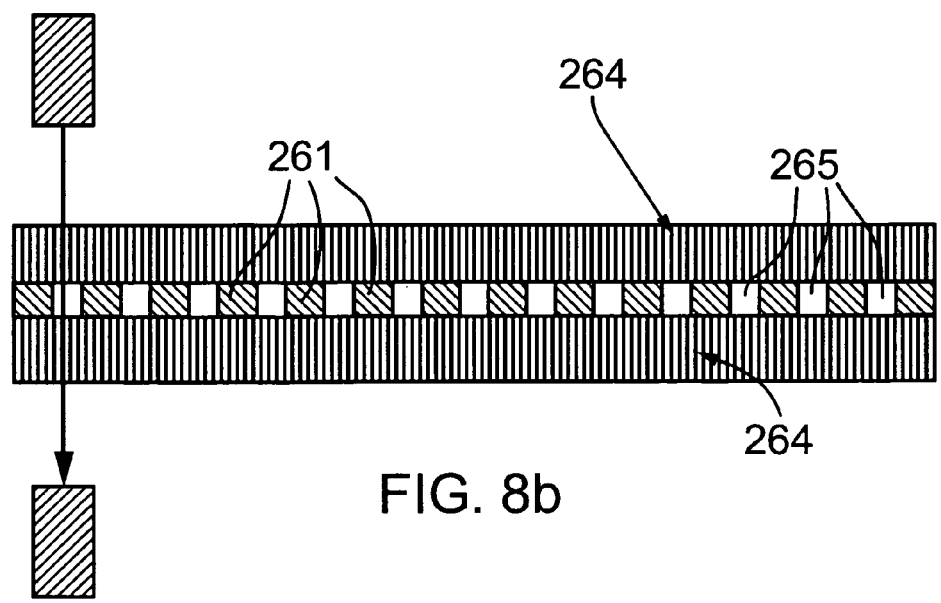

Using an optical circuit 140 similar to that seen in FIG. 4c, it is possible to consider it is possible to consider embodiments that are enabled by variations in the transmission of light through an encoder interface 140 as the imaging probe undergoes rotational motion. In FIG. 8a the transmission-based encoding interface 260 comprises a pattern of attenuating or reflective regions 261 embedded in a transmissive medium 262 that is generally transparent for the light 263 used by the encoding system. The medium can be a polymer, glass or other transmissive medium that is formed around the encoder pattern. Alternatively, two layers of transmissive media 264 can be used to sandwich the pattern of attenuating or reflective regions 261 as seen in FIG. 8b. The transparent media provide mechanical support to the otherwise thin encoder pattern, although it is possible to build an encoder pattern without the supporting media.

As light is directed towards the encoder by the emitting arm of the optical encoder circuit, the pattern of the encoder interface will only allow light through the substantially transmissive gaps 265 between the encoder's features. The detection arm of the optical encoder circuit will then direct light back towards the detection portion of the circuit. While it may not be necessary to include further optics other than the fibers themselves, the addition of lenses, spacers and/or collimators to the distal end of either arm of the fiber optic may improve the signal to noise or resolution of the encoder system.

While transmissive encoding interfaces 260 such as those shown in FIGS. 8a and 8b respectively are primarily designed for use with the optical circuit in FIG. 4c (comprising an emission arm on one side of the encoding interface and the distal end of the detection arm on the opposite side of the encoding interface) it is also possible to use a transmissive encoding interface 260 with optical circuits 100 or 120 in FIGS. 4a and 4b if the pattern of attenuating or reflective regions 261 is made of a substantially reflective material. In this configuration, light will be reflected back towards to the detection arm when a portion of the reflective material is in the path of the emitted light beam. However, the amount of light reflected back towards the detection arm will decrease when the light beam is directed towards one of the substantially transmissive gaps 265.

Interferometry-based Embodiments of the Encoding Interface

Yet another mechanism for creating a robust encoding system is to exploit interferometric means for detecting a rotation. This principle uses a concept similar to that used for implementing compact discs where a focused beam with a known spot size from a coherent light source is directed towards a reflective substrate. Indentations in the reflective substrate are designed to have an appropriate depth and width that cause the reflected light to change in amplitude when the beam travels across the indentations. The decrease in light occurs as a result of destructive interference between light that reflects from the top surface of the substrate and light that reflects from the bottom surface in the indentation. This destructive interference is most prominent when half the detected light from the beam comes from the top surface and half comes from the bottom surface and when the depth d of the indentation satisfies the equation:

$$d = i * wavelength/4, \text{ where } i \text{ is any odd integer.}$$

Note this wavelength is the wavelength in the medium of propagation of light. Therefore, for the equation above an adjustment for wavelength in air may need to be made using the refractive index for the medium of propagation.

Under this condition, light reflected from the bottom surface of the indentation would be 180 degrees out of phase with light reflected from the top surface of the encoding interface, resulting in destructive interference.

FIG. 9 shows a cross-section of an interferometric encoder interface 270 suitable for detection of rotary motion based on interferometric means. It shows a light beam 272 that is directed towards encoding interface 270 suitable for interferometric detecting of rotary motion. The indentations 274 have a bottom surface 278 offset at a prescribed depth 275 from the top surface 279 of a reflective material 271. The geometry of the indentations is selected to be suitable for creating destructive interference at several points during rotational motion of the interferometric encoder interface 270. The width 276, length (not seen in this figure as it is out of plane with the drawing surface) and spacing 277 in between indentations 274 can be tailored as necessary for a specific application, although in most cases the width 276 will be selected as the width that accommodates half the beam power when the emitted beam is centered over an indentation to produce maximal destructive interference. The interferometric encoder interface 270 can be produced using methods known in the art such as those used for manufacture of compact discs. Such methods enable production of an encoder interface for a planar surface, suitable for encoder interface bodies with a generally flat surface 501 such as encoder interface body 502 implemented as shown in FIG. 5a, but can also be adapted for use of a cylindrically shaped body such as cylindrically shaped encoder interface bodies 180 and 190 seen in FIGS. 5c and 5d.

The interferometric encoder pattern comprises a reflective material 271, such as a layer of aluminum or other reflective material, covered by a substantially transparent material 290, such as a transparent polymer, such as polycarbonate, acrylic or methylmethacrylate. A structural backing 291 may structurally support the encoder pattern.

Advantages of the interferometric method for implementing an encoder interface include potential for more efficient mass production using a stamped pattern. Alternatively, methods similar to those known in the art used for burning recordable or re-writable CDs, can be to produce a similar result.

Embodiments of the Encoding Interface Dependent on Variable Interference filters While the interferometric means outlined above depend on the use of light with a narrow bandwidth, it is possible to consider other means that depend on the use of a broad spectrum light source. Variable interference filters are filters constructed using thin film technology whereby one or more layers of the filter have a variable thickness over the length of the filter. When a broadband light source (e.g. a light source with a spectrum of light from 400 to 700 nm) is directed towards the filter, the light that is detected from the filter (either reflected back from the filter or transmitted through the filter) will have a particular wavelength of peak intensity that is function of the position of the filter through which the light propagated. Such filters are commercially available (such as a Schott Veril filter) but would have to be suitably adapted and integrated within an imaging probe for proper use to achieve the objects of the present invention. An annular variable interference filter is an example of a suitable adaptation for the present invention. Again, the interference filters could be applied using either a reflection-based configuration of the optical circuits 100 or 120 as seen in FIGS. 4a and 4b. Alternatively, a transmission-based configuration such as optical circuit 140 as seen in FIG. 4c could be used. Furthermore, the filter could be configured in a generally planar configuration with an annular shape and the light emitted in the same orientation as shown in FIG. 6a. Alternatively, it could be configured in a generally cylindrical configuration with the light emitted in the same orientation as shown in FIG. 6b or 6c.

The detection portion of the encoder circuit in such an embodiment would comprise one or more detectors such that it would be possible to detect the wavelength of peak intensity. Several such detectors exist, and include, without limitation, i) the use of a diffraction grating or prism coupled with a CCD array or an array of other photodetectors ii) the use of two or more photodetectors with different profiles of wavelength sensitivity and iii) other configurations known in the art that provide spectrometer functionality.

One advantage of a variable interference filter is that the signal detected provides the opportunity to make a direct assessment of the current angle of rotation. This is particularly true if the peak wavelength detected from the filter does not repeat itself in a single rotation of the probe. These embodiments can also provide a more direct means of identifying the direction of rotation. The angular resolution of such a system is dependent on the beam size and sensitivities of the photodetection mechanism.

FIG. 10a depicts a cross-section of a reflective variable interference encoding interface 310. Light is directed towards the interface. An optional, mechanically protective transparent layer 311 may be present. A variable interference filter comprises one or more thin film layers 312 (two shown in present diagram) that cause the light that is either reflected back or propagated forwards to be selected based on the thicknesses and dielectric properties of the thin films. A substrate 313 is used to mechanically support the thin films. For embodiments where the interference filter is selected to preferentially reflect a single wavelength that corresponds to a position along the length of the encoder interface, then the substrate 313 need not be reflective. For embodiments where the interference filter is selected to preferentially transmit a single wavelength that corresponds to a position along the length of the encoder interface, then the substrate 313 would preferably be reflective, or an additional reflective layer (not shown) would be interposed in between the substrate 313 and the bottom surface 314 of the variable interference filter 315.

FIG. 10b depicts a cross-section of a variable interference encoder interface 320 whereby the variable interference filter 315 is sandwiched in between transparent mechanically supportive media 321 to enable an embodiment that can be used in combination with an encoder circuit such as transmissive optical encoder circuit 140 as shown in FIG. 4c.

An example of the possible output of such an encoder using a variable interference filter is shown in FIG. 10c whereby the wavelength of peak intensity (along the y-axis) is shown to be a linear function of angle of rotation (along the x-axis). It is possible that, for a number of implementation specific reasons (such as light source intensities at different wavelengths, sensor sensitivities, wavelength dependent variations in attenuation in the fiber or optical components), it may be necessary to normalize or calibrate the output of the wavelength detection in order to determine the angle of rotation.

Most variable interference filters are currently constructed in a generally planar form. The predominant wavelength selected by the filter (either reflected or transmitted) is a function of the filter along a single direction (e.g. either the x-axis or y-axis of the filter) with no variation along the orthogonal direction within the plane of the filter. In order to construct a rotary encoder from such a filter, the filter can be wrapped into a cylindrical shape, whereby the axis along which the selected wavelength varies (the selective axis) is bent such that it becomes tangential to the cylinder's surface. This is suitable for the configurations of a cylindrical encoder interface body such as 170 or 189 as shown in FIGS. 5cb and 5d.

FIG. 10d depicts a configuration of a combination of two variable interference encoder interfaces 330 where two annular rings are configured concentrically to each other. The rings are both formed, such as by cutting, from a sheet of interference filter. However, the selective axis of the interference filter of the outer ring 331 is oriented at a different angle (ideally 90 degrees) from the selective axis of the inner ring 332. By using two optical encoder circuits, with one circuit detecting from the inner ring 332 to measure along one axis and the other circuit detecting from the outer ring 331 to measure along another axis, it is possible to measure two Cartesian coordinates which can be mapped to an angle of rotation.

Alternatively, a single annular encoder interface could be constructed from an interference filter material with a selective axis along a single linear dimension, but the sensitivity of the detector to rotary motion over those angles where the light beam is traversing the encoder interface at an angle perpendicular to the selective axis would be poor.

Alternatively, an annular encoder interface can be constructed whereby the thicknesses of the films in the variable interference filter vary as a function of angle from the center of the annulus, rather than along a linear dimension.

Polarization-based Embodiments of the Encoding Pattern

Yet another optical method for detection of rotary motion makes use of the polarized nature of light. A light beam can be characterized by the degree to which the light is polarized, and if it is significantly polarized, can further be characterized by the orientation of the polarization state. It is well known that if a light beam if polarized, that it is possible to modulate the intensity of the polarized light using a polarization filter. A polarization filter has a polarization axis within its plane. Light whose polarization state is not aligned with the polarization axis is attenuated preferentially over light that is aligned with the polarization axis. The amount of polarized light that can pass through a polarization filter can therefore be varied by either i) rotating the polarization state of the emitted light around an axis generally parallel to the axis of propagation or ii) by rotating the polarization filter around an axis generally parallel to the axis of propagation. This can directly be applied to measuring the angle of rotation for the purposes of the present invention. This is most applicable to encoder system embodiments where the encoder interface is configured as seen with an encoder interface body 502 as seen in FIG. 6a. Both reflective and transmissive embodiments are possible.

FIG. 11a shows a cross-section of a reflective polarization-based encoding interface body 350 whereby light exits the distal optics 115 and is emitted towards the polarization-based encoding interface. This emitted light may be polarized. The polarization of the emitted light occurs either by including a polarization filter directly into the distal optics 115 of the emitting optical circuit or by using an emitting optical fiber that maintains the polarized nature of light that propagates through it, (such as PMF polarization maintaining fiber including the PANDA fiber brand available from Fujikura, Japan). If PMF fiber is used as an alternative to using a distal polarization filter, than at some point along the arm of the optical circuit that transmits the emitted light, the light becomes polarized, such as by using a polarization filter in between the light source 122 and the proximal end of the emitting arm of the circuit.

The encoding pattern contains a polarization filter layer 352 of material that behaves as a polarization filter. An optional, transparent, protective layer 351 may cover the polarization filter layer 352. Beneath the polarization layer is a reflective surface 353 that reflects light back towards the detection arm of the optical encoder circuit. The amount of light that returns to the detection arm of the optical encoder circuit will be a function of the relative orientation of the polarized emitted light and the polarization axis of the polarization filter layer 352.

If the light is not polarized on emission from the emitter arm of the optical circuit, than the light that returns from the polarization-based encoding interface 350 to the detection circuit must pass through a second polarization filter, such as a filter within the distal detection optics 131 (i.e. if separate fibers are used for detection and emission, as seen in FIG. 4b) or along the detection arm of the optical circuit, with the additional requirement that the fiber optic that lies between the distal optics 131 of the detection arm and the detecting segment 121 of fiber optic is polarization maintaining fiber. Alternatively, the detector 126 on the detection arm of the optical encoder circuit can be replaced by a polarimeter.

FIG. 11b shows a transmissive polarization-based encoder interface 370. In this embodiment, the reflective substrate 353 in FIG. 11a is replaced with an optional transparent medium 371, thus allowing light to be transmitted to the distal optics 131 of the detection arm of the optical encoder circuit after it passes through the polarization-based encoder interface 370.

A polarization filter can be made of any material known in the art for such purposes, such as polarizing film or filters (such as Polaroid brand film), polarizing glass and wire grid linear polarizers.

Advantages of the polarization filter dependent embodiments include the fact that the rotation of the encoding pattern relative to the optical circuit components provides an inherent change in the amount of light detected that can be mapped to an angle of rotation. Furthermore, the light beam can be focused anywhere along the plane of the encoding pattern, including the intersection of the plane with the axis of rotation of the probe, and produce the same results.

FIGS. 11c through 11f pictorially depict the rotation of the polarization-based encoding interface 350 around its rotational center while the distal optics 115 of the encoder's optical circuit remain relatively fixed. In FIG. 11c, the polarization state of the light emitted from the optical circuit is aligned with polarization axis of the polarized encoding pattern. As the encoding pattern rotates, the polarization state of the emitted light and the polarization axis of the polarized encoding pattern become gradually unaligned, and this is shown to continue through to FIG. 11f. Once the polarization state of the emitted light and the polarization axis of the filter are 90 degrees out of alignment, the light detected reaches minimum. A full rotation would be represented by two peak values and two trough values of the detector output. A plot of this change over the first 90 degrees of rotation is seen in FIG. 11g whereby the detector output (on the y-axis) is a function of the angle of rotation (on the x-axis). While the FIGS. 11c through 11f have the encoder moving while the optical circuit is relatively stationary, it is possible to get the same effect by having the distal optics 115 of the optical circuit rotate around the longitudinal axis of the probe while the polarization-based encoder interface 350 is stationary, as seen in FIGS. 11h through 11k.

Optical Coherence Tomography (OCT)-Based Implementations of a Rotary Encoder

As mentioned previously, an imaging probe may include an OCT fiber to facilitate imaging of tissue. OCT has remarkably high axial resolution (on the order of 4 to 20 microns) and remarkably good lateral resolution when focused with an appropriate lens near the distal tip of the OCT imaging fiber. With the high spatial and temporal resolution afforded by OCT, it is possible to consider embodiments where an imaging probe, whether used for ultrasound imaging, OCT imaging or any other imaging method, has a separate OCT channel used primarily for the purposes of detection of rotary motion.

Any embodiments of the encoder interface 104 described for reflectance based detection (FIG. 7), transmission based detection (FIG. 8), interferometric detection (FIG. 9), and reflectance-based polarization detection could be used where the optical encoder circuit is replaced by the OCT-based encoder circuit 150 shown in FIG. 4d. To help differentiate an OCT fiber that is used in an imaging probe for the purposes of detecting rotary motion from an OCT fiber used to image tissue, a fiber used for detection of rotary motion is herein referred to as an OCT detection fiber and a fiber used for OCT imaging is herein referred to as an OCT imaging fiber.

The position of reflective boundaries in an encoder interface 104 can be easily sensed by the OCT detection system and tracked using software or hardware algorithms. As the encoder interface 104 rotates relative to the distal end of the OCT detection fiber (or vice versa), an image of the encoder interface 104 will be formed. Software or hardware-based mechanisms, such as threshold detecting mechanisms or edge detection mechanisms, can easily detect features within the OCT image of the encoder interface 104, such as the reflective encoder interface 240 seen in FIG. 7a. These detected features will be used to ascertain how much the image has rotated within a specific timeframe.

OCT fiber construction is well known in the art and is described well by Mao in the present Background. In summary, an OCT detection fiber can be made using a single mode fiber with a 125 micron or other similarly dimensioned cladding, followed by distal optics 153 comprising an optional optical spacer 202, followed by a lens, such as a GRIN lens 204 or ball lens, followed by an optional deflection mechanism 172, such as a mirror or prism.

Figure 12A:
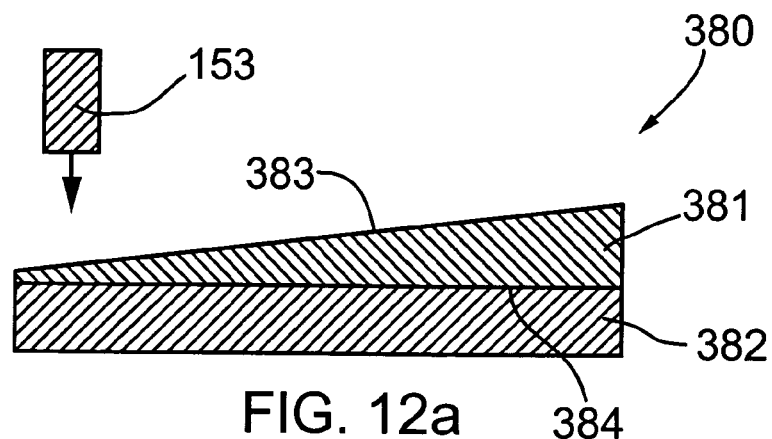
FIG. 12a shows the cross-section of encoder interface constructed to provide information regarding rotary motion as a result of being able to detect the variable thickness of an encoder interface.

Alternatively, a variable thickness encoder interface 380 can be used with an OCT-based detection circuit 150. The variable thickness encoder interface has a cross-section seen in FIG. 12a, where the thickness of an adequately transparent or translucent material varies as a function of angle. Most transparent or translucent polymers and glass materials would be adequate. The distal OCT optics 153 of an OCT-based encoder circuit 150 direct a focused beam of light to the variable thickness encoder interface 380. The OCT detection system will be able to detect reflections from the leading edge 383 and trailing edge 384 of the variable thickness material 381 and measure the thickness between at the point where the OCT beam is focused. The variable thickness material 381 could be mechanically supported by a substrate 382, which may be reflective (to enhance the detection of the trailing edge 384, but not necessarily so. A hardware or software algorithm that receives the output of the OCT detection system could then estimate the thickness and that thickness could then be mapped to an angle of rotation.

Figure 12B:
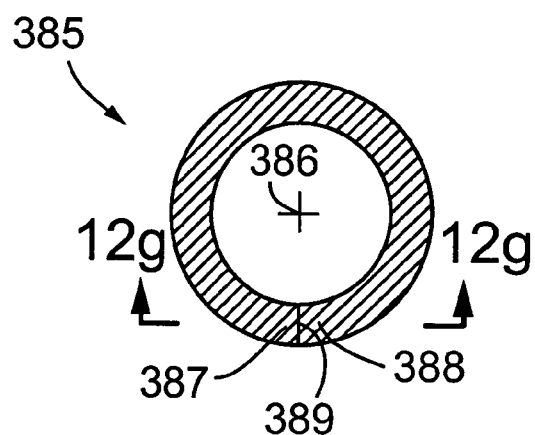
FIG. 12b shows a frontal view of an encoder interfaces constructed to provide information regarding rotary motion as a result of being able to detect the variable thickness of an encoder interface.

FIG. 12b shows an image of a variable thickness encoding interface 385 that can be incorporated with an encoder interface body's surface, such as the flat surface 501 of encoder interface body 502 in FIG. 5a. In this embodiment, the thickness is measured along an axis perpendicular to the plane of FIG. 12b. Along one angle from the geometric center 386 of the interface, the variable thickness layer is at a minimum thickness, such as near a position of minimal thickness 387. The thickness gradually increases in the counter clockwise direction until reaching a point where the variable thickness layer reaches a position of maximum thickness 388. Continuing along the clockwise direction, the thickness can transition back to the minimum thickness in a step-like manner, such as at a thickness step 389. Obviously, many variations of this embodiment could take place, such as where the transition from the minimum to maximum thickness is smooth, or where there are multiple extreme values for the thickness in a single rotation. By having multiple extreme values for the thickness in a single rotation, it may be possible to substantially increase the angular resolution of the encoding system, and one or more of the points of extreme thickness may represent an index position (e.g. a reference angle, such as 0 degrees).

Figure 12C:
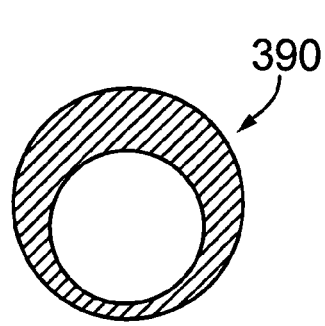
FIGS. 12c-12e show cross-sectional images of encoder interfaces constructed to provide information regarding rotary motion as a result of being able to detect the variable thickness of an encoder interface.
Figure 12D:
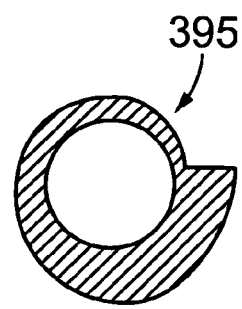
Figure 12E:
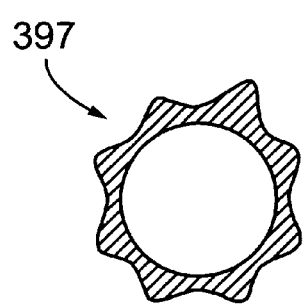
Figure 12F:
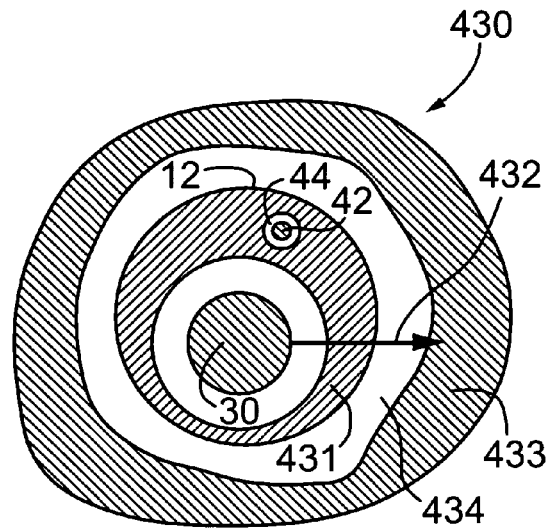
FIG. 12f shows a cross-section of an imaging probe within a patient wherein the light used for imaging the patient can also be used to provide information regarding rotary motion as a result of being able to detect the variable thickness of the walls of the probe.
Figure 12G:
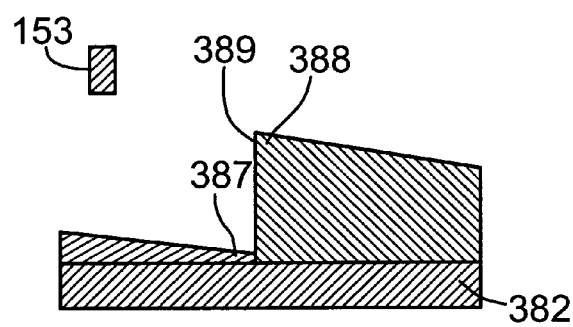
FIG. 12g shows a cross-section of the embodiment seen generally in FIG. 12b through the line 12g-12g.
Figure 13A:
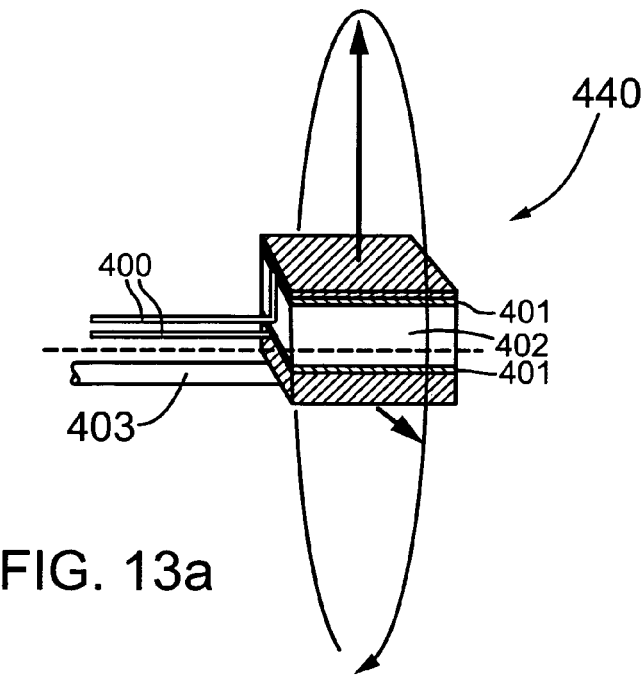
FIG. 13a is a perspective view of an imaging assembly suitable for side viewing with both acoustic and optical imaging.
Figure 13B:
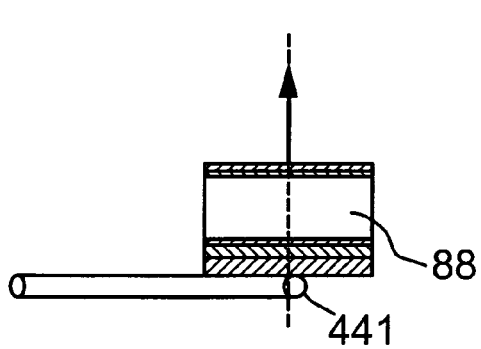
Figure 13D:
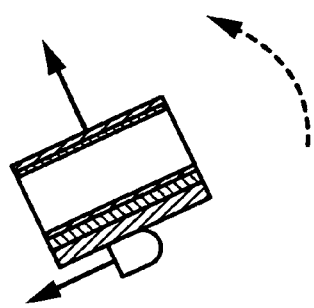
FIGS. 13c to 13e are end views of the imaging assembly in FIG. 13a in different rotated positions.
Figure 13C:
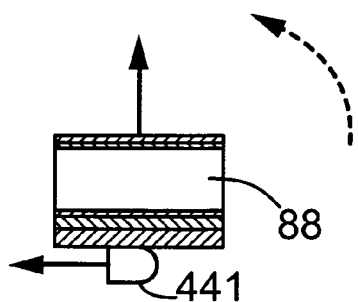
Figure 13E:
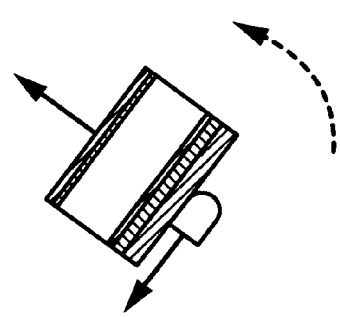

FIG. 12g provides a cross-section of line 12g-12g in FIG. 12b to better illustrate the embodiment. Distal OCT optics 153 emit light onto the variable thickness interface 385. The thickness is seen to be at a minimum at near a position of minimal thickness 387. The thickness is seen to be at a maximum near a position of maximum thickness 388. The thickness can transition back to the minimum thickness in a step-like manner, such as at a thickness step 389.

Alternatively, a variable thickness encoder interface can be mounted onto a cylindrical surface of a cylindrical encoder interface body such as the body 170 seen in FIG. 5c or the body 180 seen in FIG. 5d. FIG. 12c shows a cross-section of substantially cylindrical encoding interface 390 whereby the thickness varies smoothly and most thicknesses (except for at the thinnest and thickness points) map to two different angles of rotation. FIG. 12d shows a cross-section of a substantially cylindrical variable thickness encoding interface 395 whereby the thickness varies smoothly, except where it transitions abruptly in going from the thinnest thickness to the thickest thickness. FIG. 12e shows a substantially cylindrical encoding interface 397 whereby the thickness varies smoothly with several extreme values in the thickness, including one angle at which the thickness is greater than at any other angle, serving as an index point.

For those embodiments where the imaging probe is an OCT imaging probe, the OCT detection fiber in most of the embodiments is separate from the OCT imaging fiber. However, in some embodiments such as the combined OCT imaging and rotary encoder embodiment 430 in FIG. 12*f*, it is possible to use the same fiber optic, lens and other components for the dual purposes of imaging and detecting the angle of rotation. The shell of the imaging probe in FIG. 12F, has a variable thickness wall 431 of the imaging probe near the imaging assembly 30. The variable thickness wall 431 has the property that its thickness varies as a function of the angle from the center of the imaging probe. A single OCT imaging beam 432 can be used to serve the dual purpose of detecting the wall thickness (and thus to infer the imaging angle) and to image tissue 433 or other structures in the surrounding environment 434 outside the imaging probe 12. While many imaging probes of variable wall thickness are in existence, the method of using the OCT beam to measure the wall thickness as a marker for determining the angle of rotation is not known to have been previously described. As with the other variable thickness interfaces, the wall thickness of the imaging probe can have several extreme values. Furthermore, the guidewire lumen 44 for the guidewire 42 can be detected by the OCT beam and serve the dual purpose of an index point for the rotary encoder system.

Combinations of Encoder Components

In some instances, it may be helpful to have more than one encoding interface or more than one optical encoding circuit in order to provide a more accurate assessment of the rotational motion. As discussed above for the combination of two variable interference filter encoder interfaces 330 in FIG. 10*d*, the use of two encoding interfaces to enable the use of linear variable interference filters provides a more accurate assessment of the rotational angle. Similarly, the use of polarization-dependent interfaces may benefit from increased angular resolution with the use of more than one optical encoding circuit. For example, a first optical circuit may emit light that has a significantly different polarization state, such as a polarization state that is 45 degrees different from the polarization state of a second optical circuit.

Similarly, the use of more than one optical encoding circuit can be used to facilitate error detection, or provide a degree of redundancy.

Similarly, the use of more than one optical encoding circuit and more than one encoding interface 104 may facilitate quadrature encoding, a technique well known in the encoder art to facilitate estimation of the direction of rotation for those embodiments that do not inherently provide information about direction of rotation. Embodiments that provide direction information may be particularly helpful when the rotary motion through the torque transmission shaft is reciprocating in nature (i.e. rotates alternately between one direction and the other) rather than continuously rotating in the same direction.

Similarly, the use of more than one optical encoding circuit and more than one encoding interface may facilitate accurate assessment of the absolute angle of rotation, such as by use of Gray Code encoding, which is well known in the art.

Integration of the Features of an Encoding Pattern Onto Other Device Components

While the figures thus far have shown an encoding interface 104 to be attached to an encoder interface body 170, 180, 190 or 502 as a separate component of the imaging assembly 30, in many cases it is possible to integrate the features of an encoding interface onto another component of the imaging probe 12 or device, such as the imaging conduit 34, imaging assembly 30, external sheath 48 or any other suitable component of the imaging probe 10.

Similarly, components of the imaging probe 10 or device can serve as a substrate onto which the other features of the encoding interface 104 can be added. Possible advantages of integrating the encoding interface into other device components include reduced part counts, reduced assembly costs, improved accuracy of desired measurement and more compact design.

Use of Estimation of Rotational Motion to Remove Non-Uniform Rotational Distortion Most existing intravascular imaging instruments that comprise a rotary emitter and/or receiver acquire imaging data at a predetermined sequence, usually using a constant time interval between acquisitions of imaging data. For example, in a representative commercially available implementation of intravascular ultrasound imaging, 256 pulse/echo sequences, or vectors of data are acquired per image. The time interval between each pulse/echo sequence is equivalent to the time required for a complete revolution divided by the number of data vectors per image (e.g. 1 second divided by 30 frames per second=33 milliseconds per frame. 33 milliseconds per frame divided by 256 vectors per frame=130 microseconds per vector). In general, each vector is mapped to a sector-shaped region in the final image that spans approximately an angle of 1.4 degrees (equal to 360 degrees divided by 256). When non-uniform rotational distortion occurs, while the time interval that separates each pulse/echo sequence is constant, the true rotational angle at which the vector was acquired may be considerably less than or more than 1.4 degrees.

In the present invention, when an optical rotary encoder interface 104 is used with an appropriate optical encoding circuit, the algorithm used to time the acquisition of imaging data can be modified so that the imaging data is acquired at fixed angular intervals rather than at fixed time intervals. This algorithm may rapidly generate a signal to trigger an imaging acquisition event to occur based on output from the rotary encoder indicating that a certain increment in the angular position has occurred. Alternatively, the algorithm might generate a timing sequence based on the rotary encoding data acquired from previous revolutions of the rotary components to predict the rotational velocity and rotational position at any instant during a subsequent revolution.

Alternatively, rather than trying to generate a fixed angular interval between each event of acquiring imaging data, it is possible to collect the imaging data at a fixed time interval and use the encoder data regarding the rotational position to improve the accuracy of mapping the acquired imaging data to a displayed image. For example, with each imaging data point, the rotational angle at which the point was acquired can be stored by the imaging system. When the image is constructed for display or measurement, the measured angle information is used to produce the image rather than assuming a fixed change in angle between each imaging vector. Pixels (2D) or voxels (3D) at locations in between those pixels or voxels for which imaging data was successfully acquired can be interpolated from neighboring pixels or voxels using techniques known in the art. Alternatively, a combination of using an algorithm that attempts to image the data at predetermined angular intervals, along with the actual angular rotation observed at the time of the acquisition of the imaging data may provide a further improvement over either approach used on its own. This approach of adapting to non-uniform rotational distortion (NURD), rather than trying to circumvent NURD has the advantage of minimizing the need for certain performance characteristics of the imaging conduit such as the inclusion of a specialized torque cable. Current torque cables can limit the flexibility of an imaging probe and consume valuable space within the implementation of the probe and do not fully address the problem as NURD artifacts are often still observed in IVUS imaging probes that use specially designed torque cables.

Use of Output of Rotary Encoder to Improve Co-Registration of Multi-Modality Imaging Datasets The use of a rotary encoder may also be helpful for accurate co-registration of images by imaging probes that image in more than one direction from the longitudinal axis at a time. For example, it is possible to consider imaging assemblies 30 that image with ultrasound in one direction and OCT in another direction from approximately the same point along the length of the imaging probe 10. As the imaging assembly 30 rotates, regions imaged by the ultrasound transducer and the OCT system will overlap, but the imaging data at any point in time between the two imaging modalities will be imaged at different rotational angles. The use of a rotary encoder will improve the accuracy of the process of co-registering the ultrasound and OCT images onto each other by helping to reduce the effects of NURD.

FIGS. 13a to 13e show views of a combined modality imaging assembly 440 embodiment comprising a combined ultrasound transducer 88 and the distal end of an OCT imaging circuit 441 that both image at different rotational angles (in this example, 90 degrees apart) from each other while rotating around the longitudinal axis. Ultrasound transducer 88 comprises an acoustic substrate 402 in between conducting layers 401. The ultrasound transducer and distal end 441 of the OCT imaging fiber would be included as part of the imaging assembly 30 that rotates with the imaging conduit 34.

Further details of various combined acoustic/optical devices which may used with the encoder mechanisms disclosed herein are disclosed in copending application Ser. No. 12/010,208 filed concurrently herewith, entitled IMAGING PROBE WITH COMBINED ULTRASOUND AND OPTICAL MEANS OF IMAGING, which is incorporated herein by reference in its entirety.

Integration of Rotary Encoder into Devices with Elongate, Flexible Rotary Shafts As mentioned previously, while the present invention can specifically be used with an elongate imaging probe 12 that uses a rotary shaft such as the imaging conduit 34 as part of its scanning mechanism, its use can be generalized for use with any device that makes use of a long, flexible cable used for transmission of torque where non-uniform rotational distortion may occur and an accurate estimation of rotary motion is required. In particular, it is most suited for use with flexible torque transmission systems where the outer diameter of the torque cable is relatively small (e.g. less than 4 mm) and long (e.g. longer than 5 cm) such that conventional rotary encoding systems would not provide the desired angular resolution or be adequately compact for the intended use.

FIG. 14a demonstrates a longitudinal cross-section of the proximal and distal ends of an elongate device 450 with a torque transmission shaft 451, mechanically coupled to a torque source 452. The torque source 452 can be a motor, a handle that is manually turned by the operator or any other such device. The torque transmission shaft 452 transmits torque to the functional end 454 of the device, which can be an energy delivery device, a needle, an atherectomy head or any of several other implements. In FIG. 14c, the wall of an external sheath 453 is shown to surround the transmission shaft and is shown to enclose the functional end of the device although embodiments where the external sheath is open or has openings near the functional end are possible. An optical fiber 455 is shown to be included as part of the external sheath 453 for the purposes of enabling either the emitting light, detecting light or both to travel to or from the encoding interface 104 that is remote to the proximal end of the transmission sheath. In FIG. 14a the cylindrical encoding interface body 180 in this case is attached to a rotating portion of the device while the fiber is relatively stationary. The optical fiber 455 may be included as part of the extrusion of the external sheath 453, as shown, or may be added to the inner or outer surface of the sheath and anchored to the sheath 453 by methods well known in the art, such as bonding or surrounding the fiber and sheath with an additional layer of heat shrinkable material. The optical fiber 455 is terminated with any necessary distal optics 115, such as an optical spacer, lens and/or deflecting mechanism 172 (such as a prism or mirror) to direct light towards the encoding interface 104. The encoding interface 104 in FIG. 14a is similar to that on the cylindrical encoder interface body 170 seen in FIG. 5c. The encoding interface 104 in FIG. 14b is similar to that on the cylindrical encoder interface body 502 or 190 seen in FIG. 5a or 5e. As the encoding optical circuit used in the embodiments of FIGS. 14a and 14b are not mounted onto or directly coupled with the torque transmission shaft, there is no need for an optical rotary joint along the optical encoding circuit.

FIG. 14c shows a cross-sectional image of a representative cross-section through the device 450 in FIG. 14b through line 14c-14c. One or more fiber optics 455 for the encoding system may be incorporated with the external sheath 453.

Figure 14D:
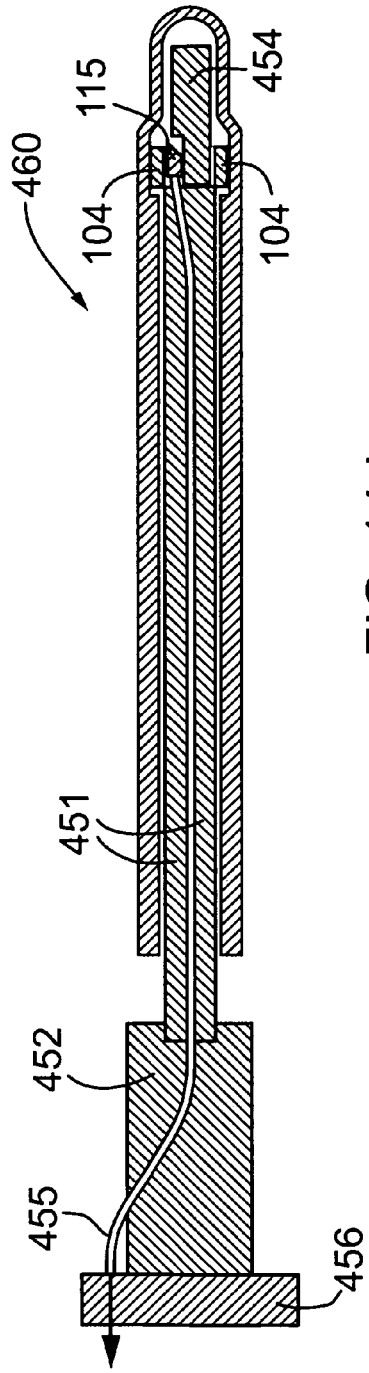

FIG. 14d shows an elongate device 460 incorporating a torque transmission shaft 451 and an optical fiber 455 of an optical encoder circuit incorporated into the torque transmission shaft 451. The encoding interface 104 is relatively stationary (shown in FIG. 14d to be attached to the external sheath) while the distal end of the optical encoder circuit including the distal optics 115 rotates with the rotary components of the device 460. The encoding pattern 104 is most similar in configuration to that shown on cylindrical encoder interface body 180 in FIG. 5d. The proximal end of the optical encoder circuit is attached to a rotary interface 456 that may contain an optical rotary joint and/or components suitable for generating or detecting light for the circuit.

Figure 14E:
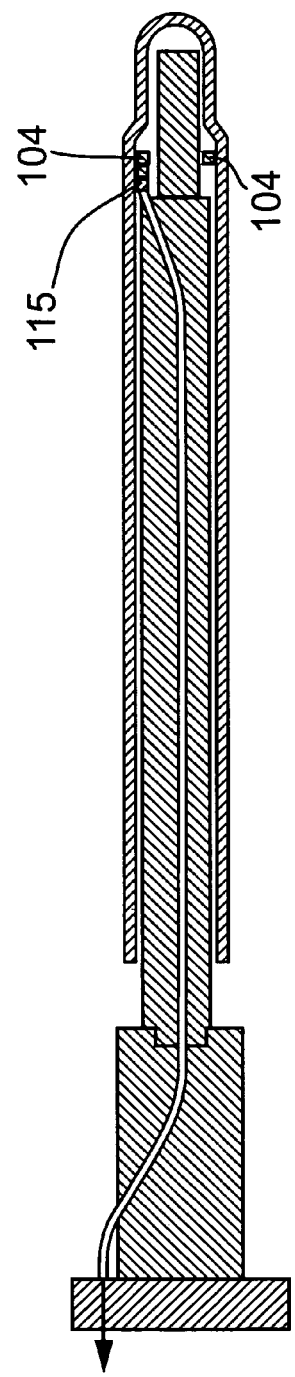

FIG. 14e shows an elongate device 470 similar to 460 with the exception that the encoding pattern 104 shown is more similar in configuration to the encoder interface body 502 in FIG. 5a. The optical fiber 455 is shown to travel along the center of the transmission shaft 451, which may provide more uniform mechanical characteristics to the transmission shaft, but it need not necessarily be aligned along the center. Near the distal end of the encoder optical circuit the optical fiber 455 is seen to bend towards the outer perimeter of the transmission shaft 451, which is helpful in several embodiments as the best angular resolution from the encoder interface 104 may be enabled by having the emitting arm emit light near the outer circumference of the encoding interface 104. While a simple bend in the fiber is one possibility to enable this configuration, a series of mirrors, or prisms in combination with additional segments of fiber optic or other light waveguide material could be used in lieu of a bend.

Integration of Rotary Encoder into an Imaging Probe

The rotary encoder embodiments can be incorporated into an imaging probe 12 by substituting the functional end of any of the embodiments in FIGS. 14a to 14e for an imaging assembly 30 and substituting the torque transmission shaft 451 for an imaging conduit 34 suitable for carrying either electrical or optical signals.

In many embodiments of imaging probes it is desirable to slide the imaging conduit 34 (which can also act as a torque transmission shaft) and the imaging assembly 30 within the external sheath. The translating along the longitudinal axis of the imaging probe 12 is referred to as a "pullback" and is commonly done to enable imaging of different regions of tissue found along a portion of the imaging probe 12 without having to move the external sheath 48. The embodiments of FIGS. 14a to 14e are limited in the sense that translating the torque transmission shaft 451 within the external sheath will cause the encoding interface 104 and the distal end of the encoding optical circuit to become misaligned.

Figure 15A:
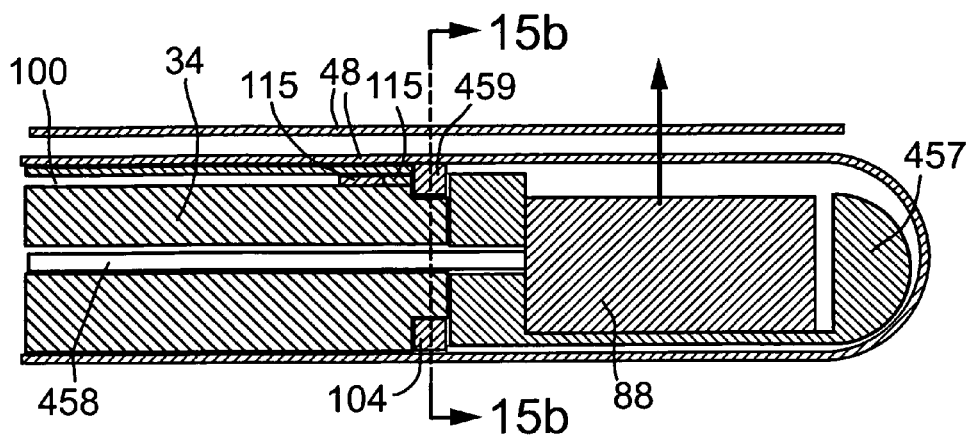
FIGS. 15a and 15c are cross sectional views of an imaging probe that incorporates an optical rotary encoder where the imaging assembly of the imaging probe can translate along the longitudinal axis of the probe.
Figure 15B:
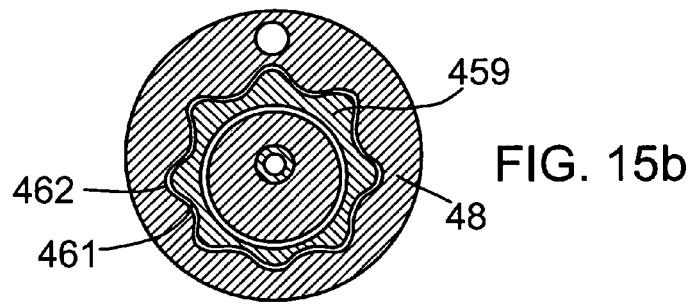
FIG. 15b is a cross-sectional view of the imaging probe in FIG. 15a through line 15b-15b.
Figure 15C:
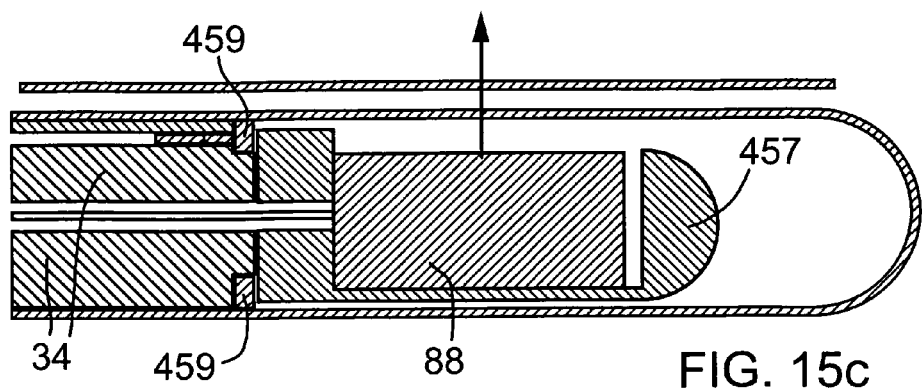

FIG. 15a depicts the distal end of an imaging probe that incorporates an encoder interface that can be pushed and pulled along the longitudinal axis of the imaging probe 12 but does not rotate with the imaging conduit 34 or imaging assembly 30. The imaging assembly 30 comprises a shell 457 and an ultrasound transducer 88. The imaging conduit 34 contains a coaxial cable 458 for providing electrical signals to the ultrasound transducer 88. The rotary encoding interface 104 is positioned in between the imaging assembly 30 and the distal end of the encoder's optical circuit 100. The substrate of the encoding interface body 459 has one or more asymmetric features 461, such as the star pattern seen in FIG. 15b that prevent it from freely rotating within the external sheath 48. The inner contour 462 of the external sheath also has an asymmetric pattern that restricts free rotational motion of the encoding interface body 459. However, the encoding interface body 459 is not directly attached to either the external sheath 48 or to the rotating components of the imaging probe 10. As the imaging conduit 34 and imaging assembly 30 are translated along the longitudinal axis of the imaging probe 12, as seen in FIG. 15c, the encoding interface body 459 moves with the rotating component such that it remains within the detection range of the distal end of the encoder's optical circuit.

FIG. 15d shows the proximal and distal ends of imaging probe 800, which comprises, a combined ultrasound and optical imaging assembly with shell 457, an encoder interface 104 and the distal end of an encoder optical circuit. The imaging assembly and imaging conduit can slide longitudinally within external sheath 48. The encoder interface 104 is of the form found on a cylindrical encoder interface body 170. The ultrasound transducer portion of the imaging assembly comprises an acoustic substrate 402, a backing material 435 and conducting layers 401. Conducting layers are connected to a coaxial cable 805 which extends through imaging conduit 34 to the rotary interface 809 near the proximal end of the probe. The optical imaging portion of the imaging assembly includes the distal end of imaging fiber optic 805, an optical spacer 803, a GRIN lens 802 and an optical deflector such as prism 801. An optional optical window 409 may also be incorporated. The imaging fiber optic extends proximally through the imaging conduit and connects to rotary interface 809 along with the coaxial cable 805.

The distal end of the encoder optical circuit comprises an optical fiber 200, an optional optical spacer 202, a GRIN lens 204 and an optical deflector such as prism 172. The optical fiber 200 extends proximally through a channel 810 in the wall of the external sheath and exits the imaging probe at opening 811. The proximal end of the optical fiber 200 is connected to the proximal end of an encoder optical circuit, such as encoder optical circuit 100 in FIG. 4a. The optical fiber 200 is desirably constructed such that its orientation around the long axis of the probe is fixed. If the optical fiber 200 need not slide within channel 810, it may be fixed by bonding or other means within channel 810. Alternatively, if the optical fiber 200 is translatable within channel 810, it may be attached to eccentric features 808 that run along the length of optical fiber 200 in order to prevent the fiber 200 from rotating within channel 810.

The embodiment 800 is advantageous in that it allows the imaging assembly 30 and imaging conduit to slide within the external sheath 48, and have rotary motion measured within, without requiring that the encoder optical circuit be connected to a rotary interface that may then further require an optical rotary joint, while preserving the ability to detect rotary motion. The ability to slide the imaging assembly within the external sheath 48 is accomplished by several means. In the first embodiment, the encoding pattern 104 is of a dimension along the longitudinal axis that is greater than or equal to the range of longitudinal translation that can occur without losing functionality of the encoder. Thus, as the imaging assembly translates, the distal end of the encoder optical circuit is adjacent to some portion of the encoding pattern and can continue to detect rotary motion.

In an alternative embodiment of preserving rotary encoder functionality while allowing translation within the external sheath 48, the distal end of the encoder optical circuit can slide along the longitudinal axis of the external sheath 48 as needed to keep the distal end of the encoder optical circuit aligned with the encoding pattern 104. Therefore, the optical fiber 200 and eccentric features 808 can be translated within channel 810. The eccentric features 808 can comprise any suitable material, such as nitinol wire. The eccentric features 808 not only make the fiber optic unable to rotate within channel 810, but they may also provide mechanical support for pushing and pulling the optical fiber 200 within the channel 810.

Several embodiments for a miniaturized optical encoder of rotary motion have been shown in the description of the present invention. Many of the encoder interfaces and mechanisms of detecting rotary motion can equally be applied to detecting longitudinal motion within an external sheath of a medical device, such as an imaging probe. Similarly, many of the encoder interfaces and mechanisms of detecting rotary motion around a longitudinal axis can equally be applied to detecting rotary motion around another axis of the imaging probe, such as a tilting axis of a tiltable component, such as where the tilting axis is orthogonal to the longitudinal axis.

FIGS. 16a and 16b show an embodiment of the imaging probe at 900 containing an encoder interface body 910 contained within sheath 48 located just behind the imaging assembly 905 for encoding the rotational position of the imaging assembly 905. Near or within the imaging assembly 905 is placed a non-rotating encoder interface body 910 that is free to travel along a portion of the length of the imaging probe. Hence, while the imaging conduit 34 and the imaging assembly 905 may rotate, the optical encoder interface body 910 does not rotate. In this example, the encoding pattern has a protruding feature 158 that is received by a similarly shaped channel along the length of the external sheath. The one or more protruding features prevent the optical encoder interface body from rotating while the adjacent imaging assembly 905 and imaging conduit 34 rotate.

A signal line within a rotating portion of the imaging probe is directed towards the encoder to facilitate reading the rotary position. In this example, an encoder circuit fiber optic 100 is included to illuminate light onto the optical encoder interface body 910 via distal optics 115. The illuminating light interacts with the optical encoder interface 104 on encoder interface body 910 in a manner that depends on the rotary angle. Light then travels from the optical encoder interface 104 back through the encoder circuit fiber optic 200. The proximal end of the fiber 200 may be connected to a photodetector or other optical transducer in the proximal end of the imaging probe and convert the light signal into one or more electrical signals that can then be communicated to the imaging system through the adapter.

In this embodiment, acoustic transducer 88 and an optical emitter are mounted within the shell of an imaging assembly 905 and send imaging energy towards a reflective tiltable component 901 that pivots around pivot point 902. A torsion spring 904 provides a restoring force that urges the reflective tiltable component 901 to pivot until it comes into contact with a first structural stop 80. The optical emitter comprises and optical imaging fiber 804, a GRIN lens 802 and a deflecting surface, such as a mirror 903.

As the imaging assembly is rotated with imaging conduit 34, the optical rotary encoder circuit will detect the rotary motion. At high rotational speeds, the reflective tiltable component 901 will tend to overcome the restoring force of the spring 904 and pivot towards stop 82. This will cause the optical and acoustic imaging beams of the present embodiment to have the property of having a variable angle of propagation with respect to the longitudinal axis of the imaging probe. As the tilting angle of the tiltable component is dependent in part on the rotational velocity of the imaging assembly 905, information provided by the optical rotary encoder can be helpful in indirectly estimating or inferring the tilting angle of the tiltable component 901.

In addition, the encoder mechanism disclosed herein may be integrated into probes using any of the scanning mechanisms disclosed in copending application Ser. No. 12/010, 206 filed concurrently herewith, entitled SCANNING MECHANISMS FOR IMAGING PROBE, which is incorporated herein by reference in its entirety.

Referring to FIG. 1 again, imaging probe 10 (which may include any of the embodiments of the acoustic and optical sensors discussed herein) and its components may be of several dimensions and properties depending on the anatomic location and purpose of use for the imaging that is enabled by the imaging probe 10. For example, for the purposes of use in the cardiovascular system, including the cardiac chambers, the imaging probe 10 would preferably be elongate and flexible, with a length ranging from 5 to 3000 mm, preferably with a length ranging from 300 mm to 1600 mm. The imaging conduit 34 and imaging assembly 30 may have a maximum cross-sectional dimension ranging from 200 microns to 10 mm, preferably ranging from 500 microns to 5 mm. An external sheath 48 may surround both the imaging conduit 34 and imaging assembly 30. This would enable the imaging conduit 34 and imaging assembly 30 to rotate within the external sheath while mechanically isolating the rotational motion of these two components from the surrounding tissues.

In yet another example, the use of the imaging probe 10 in the gastrointestinal system would typically have the imaging probe 10 being elongate and flexible, with a length ranging from 100 mm to 2000 mm and preferably in the range of 300 mm to 1500 mm. The maximum cross-sectional dimension would typically range from 3 mm to 20 mm.

In yet another example, the use of the imaging probe 10 to image soft tissue via percutaneous means would have the imaging probe with a rigid shaft. The external sheath 48 would be replaced by a rigid hollow shaft, such as a stainless steel tube although many other polymers, metals and even ceramics would be functionally suitable.

Embodiments of the present invention can be used in conjunction with or incorporated into devices that are used for intervention, such as those used for cardiovascular intervention, such as an angioplasty balloon, atherectomy device, stent delivery system or localized drug delivery system. It can also be used in conjunction with or incorporated into devices that facilitate biopsies, radio-frequency ablation, resection, cautery, localized brachytherapy, cryotherapy, laser ablation or acoustic ablation.

In particular, using the image scanning mechanism to direct higher powers of optical or acoustic energy to a targeted region can facilitate the use of the current device to enable laser or acoustic ablation of tissue. For example, while imaging a region of a blood vessel with an OCT or ultrasound embodiment of an imaging probe described in the present invention a region for the delivery of therapy can be selected through a used interface. Then, powerful pulses of energy can be delivered at times when the scanning mechanism is oriented to delivery energy in the desired direction. For example, pulses of laser energy can be transmitted down the same fiber optic used for optical imaging, be deflected by a deflecting component in those embodiments that include a deflecting component, and travel towards the targeted tissue for the desired effect. The timing of the pulses of laser energy is coordinated with the scanning pattern affected by the imaging probe 10 to direct the energy towards the targeted region.

Gastrointestinal endoscopy, colposcopy, bronchoscopy, laparoscopy, laryngoscopy, cystoscopy, otoscopy and fundoscopy are all examples of applications to which the scanning mechanisms described in the present invention may be adapted for use in a manner similar to angioscopy or infrared imaging. Non-medical uses of a flexible and/or miniaturizable imaging probe where a scanning mechanism described in this invention is used to produce an image, such as a picture taken in the visible or infrared spectrum are several.

Embodiments of the present invention can be used in conjunction with or incorporated into devices that are used for intervention, such as those used for cardiovascular intervention, such as an angioplasty balloon, atherectomy device, stent delivery system or localized drug delivery system. It can also be used in conjunction with or incorporated into devices that facilitate biopsies, radio-frequency ablation, resection, cautery, localized brachytherapy, cryotherapy, laser ablation or acoustic ablation. In particular, using the image scanning mechanism to direct higher powers of optical or acoustic energy to a targeted region can facilitate the use of the current device to enable laser or acoustic ablation of tissue. For example, while imaging a region of a blood vessel with an OCT or ultrasound embodiment of an imaging probe 10 described in the present invention a region for the delivery of therapy can be selected through a user interface. Then, powerful pulses of energy can be delivered at times when the scanning mechanism is oriented to deliver energy in the desired direction. For example, pulses of laser energy can be transmitted down the same fiber optic used for optical imaging, be deflected by a deflecting component in those embodiments that include a deflecting component, and travel towards the targeted tissue for the desired effect. The timing of the pulses of laser energy is coordinated with the scanning pattern produced by the imaging probe 10 to direct the energy towards the targeted region.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An imaging probe comprising:
an elongate outer sheath having a longitudinal axis;
a rotatable conduit housed within said elongate outer sheath, wherein said rotatable conduit is rotatable about said longitudinal axis;
an imaging assembly connected to said rotatable conduit at a location remote from a proximal end of said rotatable conduit;
a first fiber optic extending through said elongate outer sheath and having a distal end located in a proximity of said imaging assembly;
a rotary encoder including an optical encoder interface configured to interact with light, wherein one of said first fiber optic and said rotary encoder rotates in conjunction with said rotatable conduit;
wherein the optical encoder interface includes a polarization filter such that emitted light that is emitted by said first fiber optic and directed onto said optical encoder interface interacts with said polarization filter to produce encoded light having a polarization state that continuously varies under rotation of said rotatable conduit; and
wherein said first fiber optic or an additional fiber optic is configured for receiving said encoded light and directing said encoded light to a proximal end of said elongate outer sheath for detecting the encoded light.

2. The imaging probe according to claim 1 further comprising an output polarization filter for modulating an intensity of unpolarized emitted light that is transmitted through said rotary encoder and said output polarization filter prior to being collected by said additional fiber optic, wherein said output polarization filter is fixed relative to said additional fiber optic, such that an intensity of encoded light collected by said additional fiber optic varies with an angular orientation of said rotary encoder relative to said additional fiber optic.

3. The imaging probe according to claim 1 wherein said additional fiber optic is a polarization maintaining fiber optic that is configured for collecting the encoded light that is transmitted through said rotary encoder.

4. The imaging probe according to claim 1 wherein the emitted light is polarized, and wherein an intensity of encoded light that is collected by said additional fiber optic varies with an angular orientation of said rotary encoder relative to said additional fiber optic.

5. The imaging probe according to claim 4 further comprising an input filter for polarizing the emitted light, wherein said input filter is fixed in relation to said first fiber optic.

6. The imaging probe according to claim 4 wherein said first fiber optic is a polarization maintaining fiber optic.

7. The imaging probe according to claim 1 wherein said encoded light is reflected by a reflective layer within said rotary encoder prior to being collected by said first fiber optic, and wherein the first fiber optic is a polarization maintaining fiber optic.

8. The imaging probe according to claim 7 wherein the emitted light is polarized.

9. The imaging probe according to claim 1 wherein said first fiber optic, said rotary encoder and said optional additional fiber optic form a first optical circuit, said imaging probe further comprising a second optical circuit, wherein said first optical circuit and said second optical circuit are configured for encoding both angular displacement and direction of rotation.

10. An imaging probe comprising:
an elongate outer sheath having a longitudinal axis;
a rotatable conduit housed within said elongate outer sheath, wherein said rotatable conduit is rotatable about said longitudinal axis;
an imaging assembly connected to said rotatable conduit at a location remote from a proximal end of said rotatable conduit;
a first fiber optic extending through said elongate outer sheath and having a distal end located in a proximity of said imaging assembly;
a rotary encoder including an optical encoder interface configured to interact with light, wherein one of said first fiber optic and said rotary encoder rotates in conjunction with said rotatable conduit;
wherein the optical encoder interface includes a variable optical filter configured such that emitted light that is emitted by said first fiber optic and directed onto said optical encoder interface interacts with said variable optical filter to produce encoded light such that an optical spectrum of the encoded light continuously varies under rotation of said rotatable conduit; and
wherein said first fiber optic or an additional fiber optic is configured for receiving the encoded light and directing the encoded light to a proximal end of said elongate outer sheath for detecting the encoded light.

11. The imaging probe according to claim 10 wherein said variable optical filter is configured such that emitted light that is emitted by said first fiber optic and directed onto said optical encoder interface interacts with said variable optical filter to produce encoded light such that an optical spectrum of the encoded light includes an intensity peak characterized by a wavelength that continuously varies under rotation of said rotatable conduit.

12. The imaging probe according to claim 10 wherein said variable optical filter is configured as a cylindrical surface, such that a wavelength dependent direction of said variable optical filter along which a wavelength varies is a circular contour of said cylindrical surface, and wherein the emitted light is incident on said variable optical filter from a radial direction.

13. The imaging probe according to claim 10 wherein said variable optical filter is configured in a generally planar and annular shape such that the emitted light is incident on said variable optical filter from a longitudinal direction.

14. The imaging probe according to claim 13 wherein said variable optical filter is a first variable optical filter, said imaging probe further comprising a second variable optical filter configured in a generally planar and annular shape and provided such that said second variable optical filter is concentric with said first variable optical filter, and wherein a selective axis of said first variable optical filter is oriented at a different angle from a selective axis of said second variable optical filter;
wherein said first fiber optic, said rotary encoder and said optional additional fiber optic form a first optical circuit such that said rotary encoder of said first optical circuit includes said first variable optical filter; and
wherein said imaging probe further comprises a second optical circuit, wherein said rotary encoder of said second optical circuit comprises said second variable optical filter.

15. An imaging probe comprising:
an elongate outer sheath having a longitudinal axis;
a rotatable conduit housed within said elongate outer sheath, wherein said rotatable conduit is rotatable about said longitudinal axis;

an imaging assembly connected to said rotatable conduit at a location remote from a proximal end of said rotatable conduit;

a single mode fiber optic extending through said elongate outer sheath and having a distal end located in a proximity of said imaging assembly;

a rotary encoder including an optically transparent annular encoder interface, wherein a thickness of said annular encoder interface, as determined in a longitudinal direction, varies with azimuthal angle, and wherein one of said fiber optic and said rotary encoder rotates in conjunction with said rotatable conduit;

wherein said rotary encoder is configured such that emitted light that is emitted, in a longitudinal direction, by said fiber optic, is transmitted through said annular encoder interface, thereby producing encoded light including first encoded light that is reflected from a front surface of said annular encoder interface and second encoded light that is reflected from a back surface of said annular encoder interface, such that an angle dependent thickness of said annular encoder interface is encoded by said encoded light; and wherein said fiber optic is configured for receiving said encoded light and directing said encoded light to an external optical coherence detection system for inferring rotational motion of said rotatable conduit based on said encoded light.

16. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a gradient refractive index (GRIN) lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light; and
wherein said first fiber optic or an additional fiber optic is configured for receiving the encoded light and directing the encoded light to a proximal end of said elongate external sheath for detecting the encoded light.

17. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said rotary encoder includes an optically transmissive protective layer covering said light interaction features.

18. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said rotary encoder includes a reflective surface, wherein said light interaction features are offset features in said reflective surface, wherein each offset feature has an offset from said reflective surface approximately equal to an odd number of quarter wavelengths of the emitted light, and wherein the emitted light is directed onto said rotary encoder with sufficient resolution such that the emitted light is focused onto one indentation at a time during rotation of said rotatable conduit.

19. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;

a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said rotary encoder includes an interferometric encoder interface.

20. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said light interaction features include reflective or attenuating portions adjacent to transmissive gaps, such that the encoded light includes transmitted light that is transmitted through said transmissive gaps, and wherein said additional fiber optic is configured for collecting the transmitted light.

21. The imaging probe according to claim 20 further comprising a reflective and optical displacement means for laterally displacing the emitted light or the transmitted light beyond a radial extent of said rotary encoder and reflecting the emitted light or the transmitted light for collection by said additional fiber optic.

22. The imaging probe according to claim 21 wherein said reflective and optical displacement means is configured to redirect the transmitted light over a dimension that is smaller than a minimum bend radius of said first fiber optic or said additional fiber optic.

23. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said light interaction features are provided on a longitudinally oriented surface of said rotary encoder, such that the emitted light is incident on said rotary encoder from a longitudinal direction.

24. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said rotary encoder includes a cylindrical surface and said light interaction features are provided on said cylindrical surface such that the emitted light is incident on said rotary encoder from a radial direction, said imaging probe further including an optical deflection element in optical communication with said lens for deflecting the emitted light onto said light interaction features.

25. The imaging probe according to claim 24 wherein said light interaction features are provided on an outer radial surface of a cylindrical member, and wherein said cylindrical member is configured to rotate with said rotatable conduit.

26. The imaging probe according to claim 24 wherein said cylindrical surface is an inner cylindrical surface, and wherein said first fiber optic is configured to rotate with said rotatable conduit.

27. The imaging probe according to claim 24 wherein said light interaction features are provided over a longitudinal extent of said cylindrical surface such that said rotary encoder is translatable relative to said first fiber optic over said longitudinal extent while maintaining alignment between said rotary encoder and said first fiber optic.

28. The imaging probe according to claim 27 wherein fiber optic is slidable in a longitudinal direction relative to said external sheath for maintaining alignment of said first fiber optic with said rotary encoder.

29. The imaging probe according to claim 28 wherein said elongate external sheath includes a channel for receiving said first fiber optic, and wherein said channel further comprises one or more longitudinal support structures attached to said first fiber optic for preventing rotation of said first fiber optic when sliding said first fiber optic.

30. The imaging probe according to claim 29 wherein said one or more longitudinal support structures comprise one or more nitinol shafts.

31. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said first fiber optic is connected to said rotatable conduit and wherein said external sheath and said rotary encoder include a rotation restriction means for restricting said rotary encoder from undergoing free rotation when said rotatable conduit is rotated, and wherein said rotary encoder is positioned between said imaging assembly and a distal portion of said rotatable conduit, and wherein said rotary encoder is unattached to said rotatable conduit and to said elongate external sheath, such that a longitudinal translation of said rotatable conduit produces a corresponding longitudinal translation of said rotary encoder.

32. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and
wherein said first fiber optic is connected to said rotatable conduit and wherein said external sheath and said rotary encoder include a rotation restriction means for restricting said rotary encoder from undergoing free rotation when said rotatable conduit is rotated, and wherein said rotary encoder is received within a radial groove in a distal portion of said rotatable conduit, and wherein said rotary encoder is unattached to said rotatable conduit and said elongate external sheath, such that a longitudinal translation of said rotatable conduit produces a corresponding longitudinal translation of said rotary encoder.

33. An imaging probe comprising:
an elongate external sheath having a longitudinal axis;
a rotatable conduit housed within said elongate external sheath, wherein said rotatable conduit is rotatable about said longitudinal axis;
an imaging assembly connected to said rotatable conduit at a location remote from a proximal end of said rotatable conduit;
a first fiber optic extending through said elongate external sheath and having a distal end located in a proximity of said imaging assembly;
a lens optically coupled to said distal end of said first fiber optic; and
a rotary encoder including a plurality of light interaction features, wherein one of said first fiber optic and said rotary encoder rotates in conjunction with said rotatable conduit;
wherein said rotary encoder is configured such that emitted light that is emitted by said first fiber optic is directed, by said lens, onto said features of said rotary encoder during rotation of said rotatable conduit with sufficient resolution such that the emitted light is focused onto one feature at a time during rotation of said rotatable conduit, thereby producing encoded light;
wherein said first fiber optic or an additional fiber optic is configured for receiving the encoded light and directing the encoded light to a proximal end of said elongate external sheath for detecting the encoded light; and wherein said first fiber optic, said lens, said rotary encoder and said optional additional fiber optic form a first optical circuit, said imaging probe further comprising a second optical circuit, wherein said first optical circuit and said second optical circuit are configured for encoding both angular displacement and direction of rotation.

* * * * *